(12) United States Patent
White et al.

(10) Patent No.: US 12,121,271 B2
(45) Date of Patent: Oct. 22, 2024

(54) FEMORAL FIXATION DEVICES, SYSTEMS, AND METHODS

(71) Applicant: RTG Scientific, LLC, Austin, TX (US)

(72) Inventors: Raymond White, Windham, ME (US); Matthew Camuso, Falmouth, ME (US); Corey Johnson, Rochester, MN (US); Andrew Fauth, North Logan, UT (US)

(73) Assignee: RTG Scientific, LLC, Austin, TX (US)

( * ) Notice: Subject to any disclaimer, the term of this patent is extended or adjusted under 35 U.S.C. 154(b) by 338 days.

(21) Appl. No.: 17/468,806

(22) Filed: Sep. 8, 2021

(65) Prior Publication Data
US 2022/0249147 A1 Aug. 11, 2022

Related U.S. Application Data

(60) Provisional application No. 63/147,640, filed on Feb. 9, 2021.

(51) Int. Cl.
*A61B 17/86* (2006.01)
*A61B 17/74* (2006.01)

(52) U.S. Cl.
CPC .......... *A61B 17/746* (2013.01); *A61B 17/744* (2013.01); *A61B 17/863* (2013.01); *A61B 17/8645* (2013.01); *A61B 2017/8655* (2013.01)

(58) Field of Classification Search
CPC ... A61B 17/742; A61B 17/744; A61B 17/746; A61B 17/863; A61B 2017/8655
See application file for complete search history.

(56) References Cited

U.S. PATENT DOCUMENTS 3,374,786 A * 3/1968 Callender, Jr. ....... A61B 17/746
    606/65
3,842,825 A * 10/1974 Wagner .............. A61B 17/8863
    606/104

(Continued)

FOREIGN PATENT DOCUMENTS

GB        2033755 A     5/1980
WO   2004098442 A1   11/2004
(Continued)

OTHER PUBLICATIONS

International Search Report dated Aug. 10, 2023 for corresponding PCT/US2023/020900.
(Continued)

*Primary Examiner* — Julianna N Harvey
(74) *Attorney, Agent, or Firm* — David Meibos; Maywood IP Law

(57) ABSTRACT

A femoral fixation device may include a shaft and a helical thread disposed about the shaft between a first location and a second location along the shaft. The helical thread may include a concave undercut surface. The femoral fixation device may be configured such that, when the femoral fixation device is implanted within a neck and a head of a femoral bone: the first location, the second location, and the helical thread therebetween may be disposed within the head of the femoral bone; the concave undercut surface may be oriented toward a proximal end of the femoral fixation device; and the concave undercut surface may be configured to transmit at least one force from the head of the femoral bone to the neck of the femoral bone.

31 Claims, 27 Drawing Sheets

(56) References Cited

U.S. PATENT DOCUMENTS

| | | | |
|---|---|---|---|
| 3,848,276 A | 11/1974 | Martinez | |
| 4,488,543 A * | 12/1984 | Tornier | A61B 17/746 606/65 |
| 4,810,149 A | 3/1989 | Lee et al. | |
| 5,356,410 A * | 10/1994 | Pennig | A61B 17/746 606/62 |
| 5,514,138 A * | 5/1996 | McCarthy | A61B 17/746 606/65 |
| 5,964,768 A | 10/1999 | Huebner | |
| 6,800,078 B2 | 10/2004 | Reed | |
| 7,537,603 B2 | 5/2009 | Huebner et al. | |
| 8,337,205 B2 | 12/2012 | Reed | |
| 8,602,781 B2 | 12/2013 | Reed | |
| 8,875,399 B2 | 11/2014 | Reed | |
| 9,079,263 B2 | 7/2015 | Reed | |
| 9,526,547 B2 | 12/2016 | Reed | |
| 9,687,319 B2 | 6/2017 | Reed | |
| 9,782,209 B2 | 10/2017 | Reed | |
| 9,901,379 B2 | 2/2018 | Reed | |
| 10,085,782 B2 | 10/2018 | Reed | |
| 10,265,177 B2 | 4/2019 | Quinn et al. | |
| 10,441,385 B2 | 10/2019 | Reed | |
| 10,639,086 B2 | 5/2020 | Reed | |
| 10,687,877 B2 | 6/2020 | Lavigne et al. | |
| 2003/0088248 A1 | 5/2003 | Reed | |
| 2006/0189987 A1 * | 8/2006 | Orbay | A61B 17/8888 606/62 |
| 2006/0204930 A1 | 9/2006 | Sul | |
| 2007/0233123 A1 | 10/2007 | Ahmad et al. | |
| 2009/0069852 A1 | 3/2009 | Farris et al. | |
| 2009/0305189 A1 | 12/2009 | Scortecci et al. | |
| 2010/0094358 A1 | 4/2010 | Moore et al. | |
| 2010/0121327 A1 * | 5/2010 | Velikov | A61B 17/744 606/301 |
| 2011/0288650 A1 | 11/2011 | Ries et al. | |
| 2013/0253517 A1 | 9/2013 | Mitchell et al. | |
| 2014/0023990 A1 | 1/2014 | Zadeh | |
| 2014/0053696 A1 * | 2/2014 | Reed | B23G 1/02 82/1.11 |
| 2014/0056460 A1 | 2/2014 | Barnes | |
| 2014/0058460 A1 | 2/2014 | Reed | |
| 2014/0329202 A1 | 11/2014 | Zadeh | |
| 2018/0303529 A1 | 10/2018 | Zastrozna | |
| 2018/0335070 A1 | 11/2018 | May | |
| 2019/0038426 A1 | 2/2019 | Ek | |
| 2019/0105131 A1 | 4/2019 | Barton et al. | |
| 2019/0223917 A1 | 7/2019 | Gray et al. | |
| 2019/0358039 A1 | 11/2019 | Ducharme et al. | |
| 2021/0259842 A1 * | 8/2021 | Feng | A61B 17/7001 |
| 2022/0249148 A1 | 8/2022 | Hyer et al. | |

FOREIGN PATENT DOCUMENTS

| | | | |
|---|---|---|---|
| WO | 2007074498 A2 | 7/2007 | |
| WO | WO-2019238085 A1 * | 12/2019 | A61B 17/0401 |
| WO | 2020224657 A1 | 11/2020 | |

OTHER PUBLICATIONS

International Search Report dated Jul. 5, 2023 for corresponding PCT/US2023/018561.
International Search Report and Written Opinion dated Jul. 6, 2022 for corresponding PCT Application No. PCT/US2022/015866.
International Search Report and Written Opinion dated Apr. 25, 2022 for corresponding PCT Application No. PCT/US2021/060196.

* cited by examiner

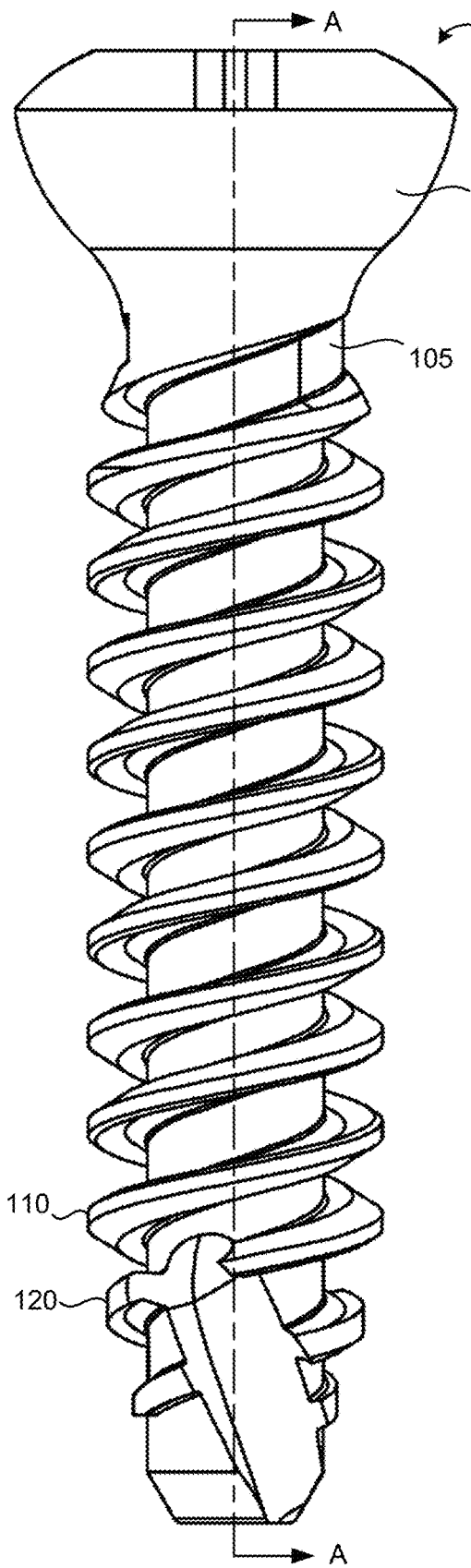
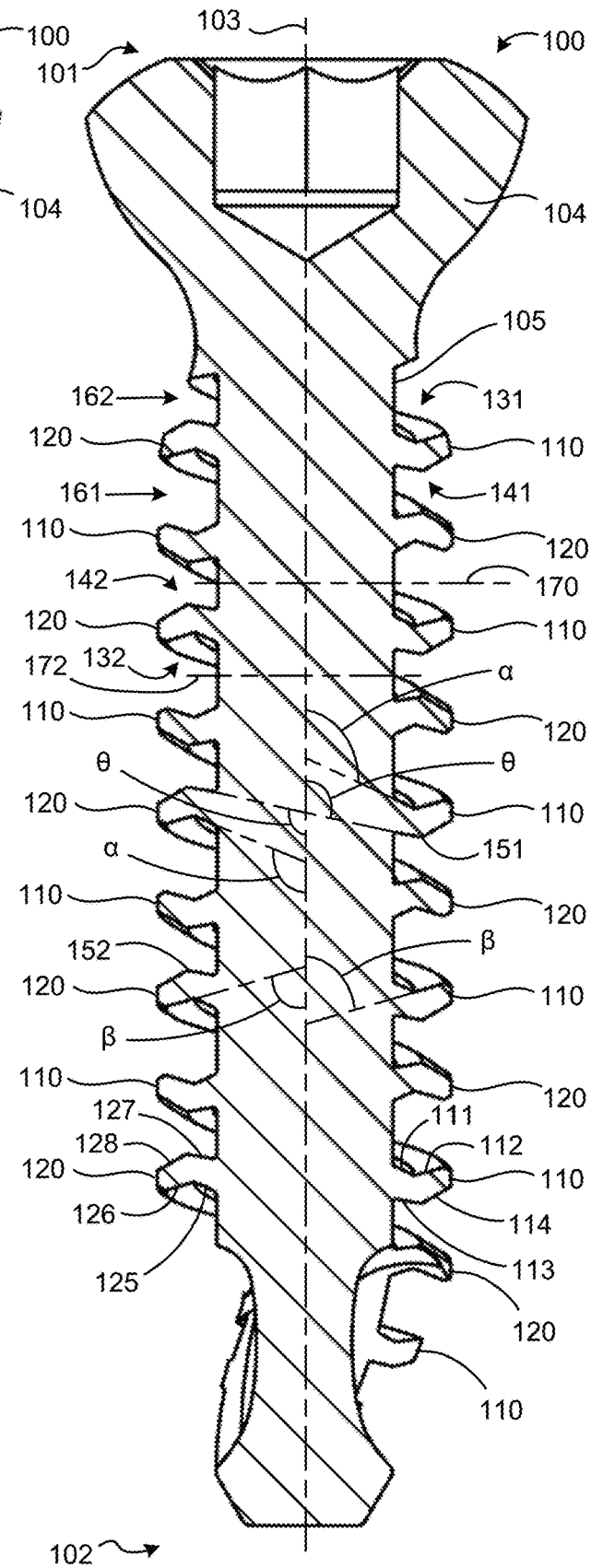
FIG. 1C  FIG. 1D

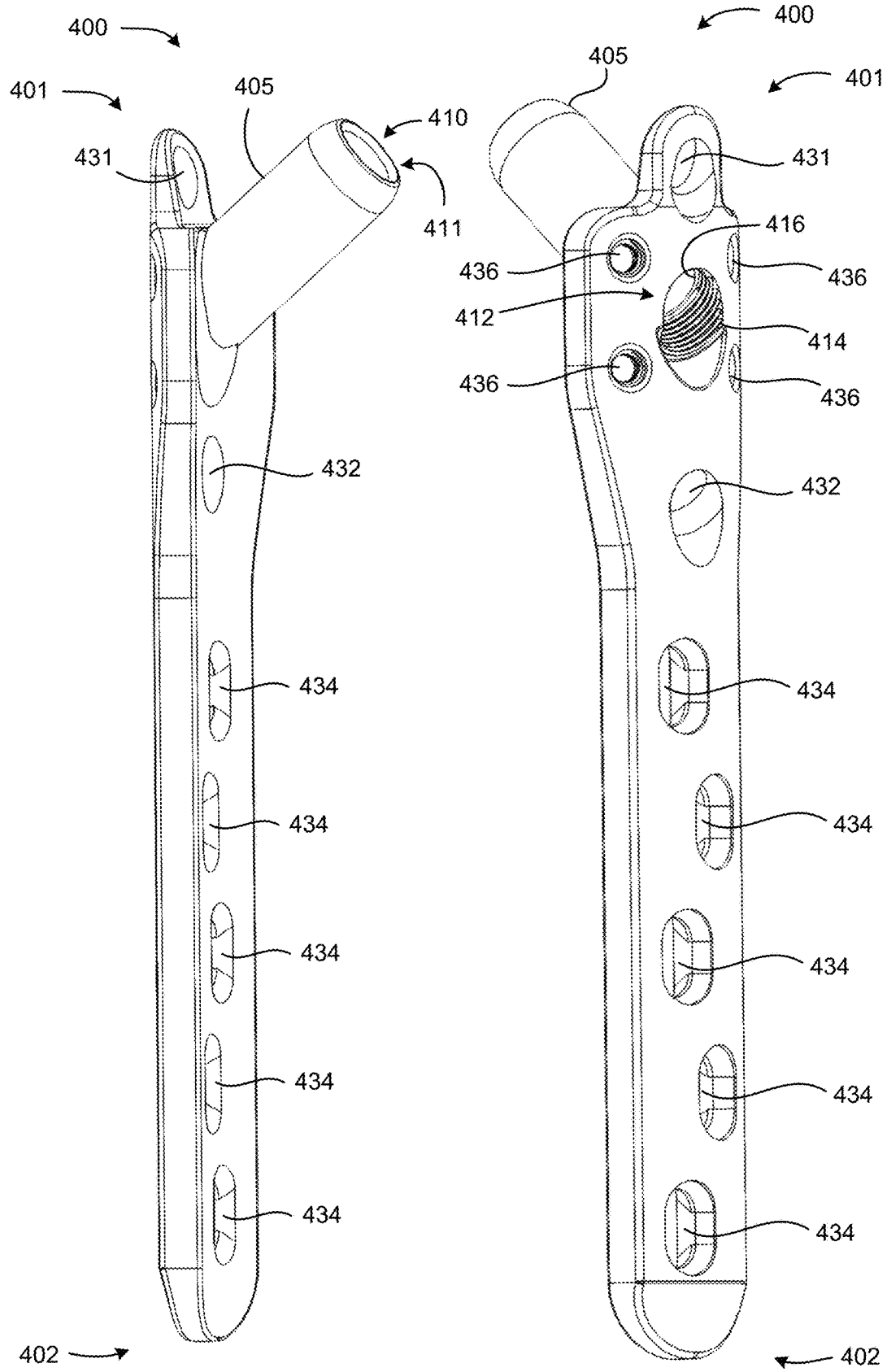
FIG. 4A  FIG. 4B

FEMORAL FIXATION DEVICES, SYSTEMS, AND METHODS

CROSS-REFERENCE TO RELATED APPLICATIONS

This application claims the benefit of U.S. Provisional Patent Application Ser. No. 63/147,640 filed on Feb. 9, 2021, entitled "FASTENING DEVICES, SYSTEMS, AND METHODS".

The foregoing are incorporated by reference as though set forth herein in their entirety.

TECHNICAL FIELD

The present disclosure relates to fixation devices, systems, and methods. More specifically, the present disclosure relates to femoral fixation devices, systems, and methods with improved fixation.

BACKGROUND

Surgical procedures involving femoral fasteners implanted in bone and other tissues can become lose over time due to multi-axial forces and off-axis loading scenarios that may be applied to the femoral fastener during the healing process. Traditional femoral fastener thread designs may not provide sufficient fixation to overcome these multi-axial forces and off-axis loading scenarios.

Accordingly, femoral fasteners with improved thread designs for increasing bone fixation and load sharing between a bone/fastener interface experiencing multi-axial and off-loading conditions would be desirable.

SUMMARY

The various femoral fastening devices, systems, and methods of the present disclosure have been developed in response to the present state of the art, and in particular, in response to the problems and needs in the art that have not yet been fully solved by currently available femoral fastening devices, systems, and methods. In some embodiments, the femoral fastening devices, systems, and methods of the present disclosure may provide improved fixation and load sharing between a bone/fastener interface under multi-axial and off-loading conditions.

In some embodiments, a femoral fixation device may include a shaft having a proximal end, a distal end, and a longitudinal axis. The femoral fixation device may also include a helical thread disposed about the shaft along the longitudinal axis between a first location and a second location along the shaft. The helical thread may include a first undercut surface and a second undercut surface. The femoral fixation device may be configured such that, when the femoral fixation device is implanted within a neck and a head of a femoral bone: (1) the first location, the second location, and the helical thread therebetween may be disposed within the head of the femoral bone; (2) the first undercut surface may be angled towards one of the proximal end and the distal end of the shaft; (3) the second undercut surface may be angled towards the other one of the proximal end and the distal end of the shaft; and (4) the first and second undercut surfaces may be configured to transmit at least one force from the head of the femoral bone to the neck of the femoral bone.

In some embodiments of the femoral fixation device, the first undercut surface may be angled towards the proximal end of the shaft and the second undercut surface may be angled towards the distal end of the shaft.

In some embodiments of the femoral fixation device, when the femoral fixation device is viewed in section along a plane intersecting the longitudinal axis of the shaft, the helical thread may include at least one chevron shape oriented toward the proximal end of the shaft.

In some embodiments of the femoral fixation device, the helical thread may include a plurality of chevron shapes oriented toward the proximal end of the shaft.

In some embodiments of the femoral fixation device, when the femoral fixation device is viewed in section along a plane intersecting the longitudinal axis of the shaft, the helical thread may include at least one partial crescent shape oriented toward the proximal end of the shaft.

In some embodiments of the femoral fixation device, the helical thread may include a plurality of partial crescent shapes oriented toward the proximal end of the shaft.

In some embodiments of the femoral fixation device, the proximal end of the shaft may include a headless cylindrical shape.

In some embodiments, a femoral fixation assembly may include a femoral fastener and a femoral support member. The femoral fastener may include a shaft having a proximal end, a distal end, and a longitudinal axis. The femoral fastener may also include a helical thread disposed about the shaft along the longitudinal axis between a first location and a second location along the shaft. The helical thread may include a concave undercut surface. The femoral support member may include a proximal end, a distal end, a longitudinal axis, and a passageway formed through the femoral support member at an angle with respect to the longitudinal axis of the femoral support member. In some embodiments, when the femoral fastener is implanted within a neck and a head of a femoral bone and the femoral support member is implanted along a longitudinal axis of the femoral bone, at least a portion of the shaft may be slidingly received within the passageway of the femoral support member, and the concave undercut surface may be oriented toward the proximal end of the femoral fastener and configured to transmit at least one force from the head of the femoral bone to the neck of the femoral bone.

In some embodiments of the femoral fixation assembly, the concave undercut surface may include at least one substantially flat surface.

In some embodiments of the femoral fixation assembly, the concave undercut surface may include a plurality of flat surfaces that are angled relative to each other.

In some embodiments of the femoral fixation assembly, when the femoral fastener is viewed in section along a plane intersecting the longitudinal axis of the shaft, the concave undercut surface may include at least one chevron shape oriented toward the proximal end of the shaft.

In some embodiments of the femoral fixation assembly, the concave undercut surface may include at least one curved surface.

In some embodiments of the femoral fixation assembly, when the femoral fastener is viewed in section along a plane intersecting the longitudinal axis of the shaft, the concave undercut surface may include at least one partial crescent shape oriented toward the proximal end of the shaft.

In some embodiments of the femoral fixation assembly, when the femoral fastener is viewed in section along a plane intersecting the longitudinal axis of the shaft, the concave undercut surface may include at least one bent shape having an intermediate portion that is oriented toward the proximal end of the femoral fastener.

In some embodiments, a femoral fixation assembly may include a femoral fastener, a femoral support member, and a stop member. The femoral fastener may include a shaft having a proximal end, a distal end, and a longitudinal axis. The femoral fastener may include a helical thread disposed about the shaft along the longitudinal axis between a first location and a second location along the shaft. The femoral support member may include a proximal end, a distal end, a longitudinal axis, and a passageway. The passageway may include a first opening and a second opening opposite the first opening. The passageway may be formed through the femoral support member at an angle with respect to the longitudinal axis of the femoral support member. The stop member may include a proximal end, a distal end, a longitudinal axis, and a stop member projection having a preselected length. In some embodiments, when the femoral fastener is implanted within a neck and a head of a femoral bone, and the femoral support member is oriented with respect to a longitudinal axis of the femoral bone: (1) at least a portion of the shaft may be slidingly received within the passageway through the first opening; (2) at least a portion of the stop member may be received within the passageway through the second opening; and (3) a space having a predetermined length may be formed within the passageway between the distal end of the stop member and the proximal end of the shaft based on the preselected length of the stop member projection.

In some embodiments of the femoral fixation assembly, the femoral support member may be a bone plate.

In some embodiments of the femoral fixation assembly, the femoral support member may be an intramedullary nail.

In some embodiments of the femoral fixation assembly, the angle of the passageway with respect to the longitudinal axis of the femoral support member may be an acute angle.

In some embodiments of the femoral fixation assembly, the predetermined length of the space within the passageway may be greater than zero.

In some embodiments of the femoral fixation assembly, the predetermined length of the space within the passageway may be zero.

In some embodiments, a method of implanting a femoral fixation device within a femoral bone may include forming a bone tunnel through a neck of the femoral bone and into a head of the femoral bone, and inserting the femoral fixation device into the bone tunnel. The femoral fixation device may include a shaft having a proximal end, a distal end, and a longitudinal axis. The femoral fixation device may also include a helical thread disposed about the shaft between a first location and a second location along the shaft. The helical thread may include a concave undercut surface oriented toward the proximal end of the shaft. The method may also include placing a portion of the shaft comprising the helical thread within the head of the femoral bone such that the concave undercut surface may be positioned to transmit at least one force from the head of the femoral bone to the neck of the femoral bone.

In some embodiments, the method may also include forming a tapped bone thread about the bone tunnel that may be configured to receive the helical thread therein.

In some embodiments of the method, placing the portion of the shaft comprising the helical thread within the head of the femoral bone further may further include rotating the shaft to insert the helical thread into the tapped bone thread disposed about the bone tunnel.

In some embodiments, the method may also include inserting the proximal end of the shaft into a first opening of a passageway formed through a femoral support member that is oriented with respect to a longitudinal axis of the femoral bone.

In some embodiments, the method may also include inserting a distal end of a stop member into a second opening of the passageway opposite the first opening, and forming a space having a predetermined length within the passageway between the distal end of the stop member and the proximal end of the shaft based on a preselected length of the stop member.

These and other features and advantages of the present disclosure will become more fully apparent from the following description and appended claims, or may be learned by the practice of the devices, systems, methods, and instruments set forth hereinafter.

BRIEF DESCRIPTION OF THE DRAWINGS

Exemplary embodiments of the present disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through use of the accompanying drawings in which:

FIG. 1C illustrates a side view of the fastener of FIG. 1A;

FIG. 1D illustrates a cross-sectional side view of the fastener of FIG. 1C, taken along the line A-A;

FIG. 4A illustrates perspective side view of a femoral support member, according to an embodiment of the present disclosure;

FIG. 4B illustrates another perspective side view of the femoral support member of FIG. 4A;

Figure 1A:
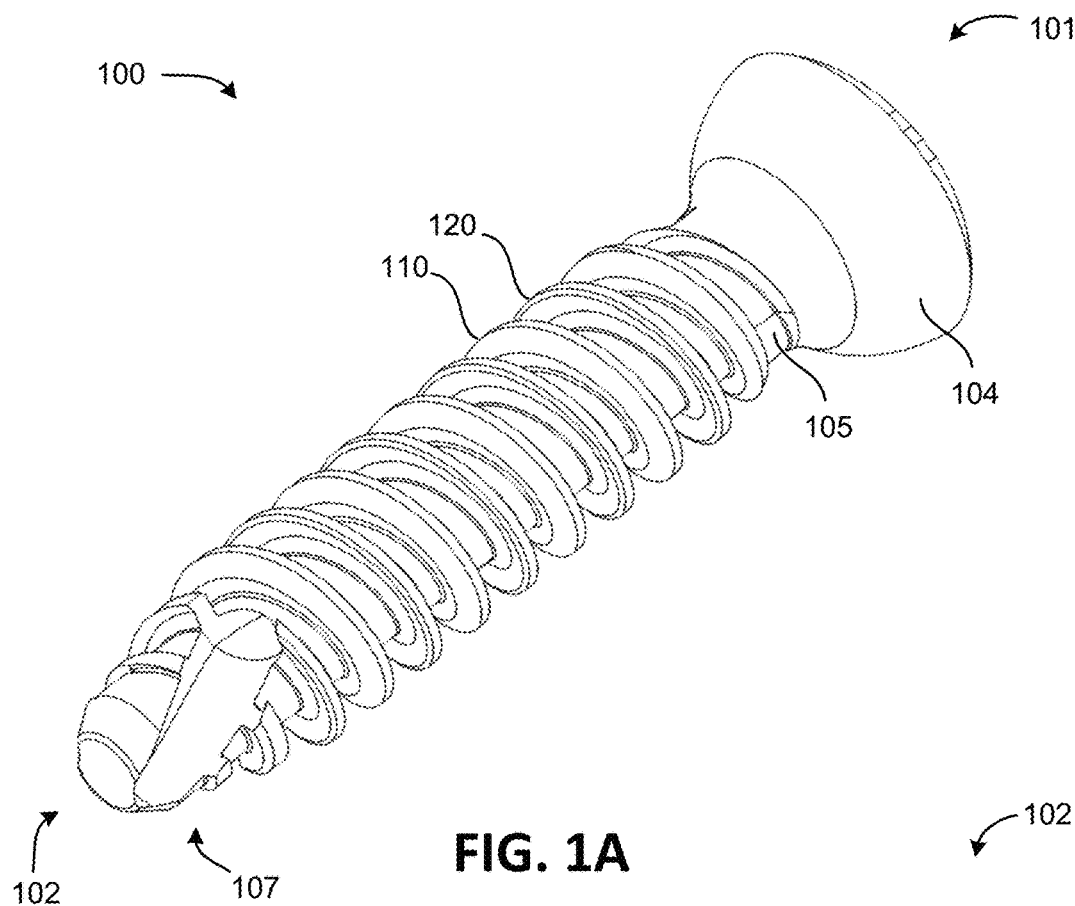
FIG. 1A illustrates a front perspective view of a fastener, according to an embodiment of the present disclosure.

It is to be understood that the drawings are for purposes of illustrating the concepts of the present disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the devices, systems, and methods, as represented in the drawings, is not intended to limit the scope of the present disclosure, but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

Figure 1B:
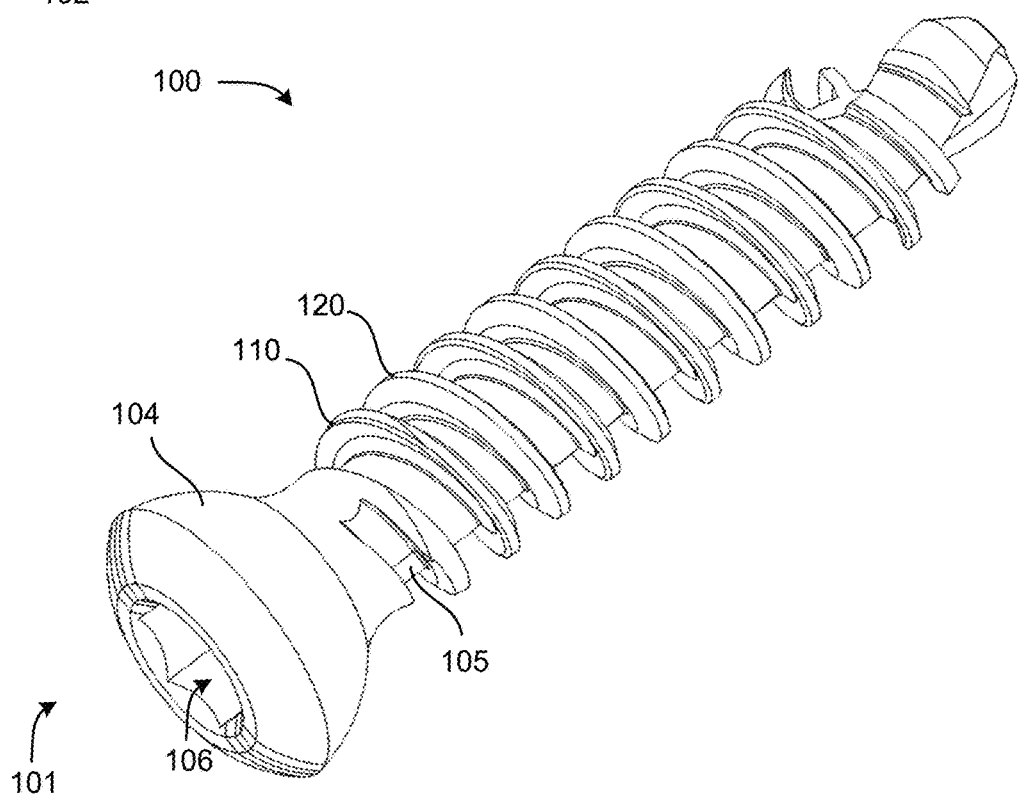
FIG. 1B illustrates a rear perspective view of the fastener of FIG. 1A.

FIGS. 1A-D illustrate various views of a fastener 100, implantable bone anchor, or bone screw, according to an example of the present disclosure. Specifically, FIG. 1A is a front perspective view of the fastener 100, FIG. 1B is a rear perspective view of the fastener 100, FIG. 1C is a side view of the fastener 100, and FIG. 1D is a cross-sectional side view of the fastener 100 taken along the line A-A in FIG. 1C.

In general, the fastener 100 may include a shaft 105 having a proximal end 101, a distal end 102, and a longitudinal axis 103. The fastener 100 may also include a head 104 located at the proximal end 101 of the shaft 105, a torque connection interface 106 formed in/on the head 104 (in either a male/female configuration), and a self-tapping feature 107 formed in the distal end 102 of the shaft 105.

In some embodiments, the fastener 100 may include a first helical thread 110 disposed about the shaft 105, and a second helical thread 120 disposed about the shaft 105 adjacent the first helical thread 110.

In some embodiments, the fastener 100 may include a "dual start" or "dual lead" thread configuration comprising the first helical thread 110 and the second helical thread 120.

In some embodiments, a depth of the first helical thread 110 and/or the second helical thread 120 with respect to the shaft 105 may define a major diameter vs. a minor diameter of the shaft 105 alone.

In some embodiments, a major diameter and/or a minor diameter of the fastener 100 may be constant or substantially constant along the entire length of the fastener, or along a majority of the length of the fastener. In these embodiments, a constant minor diameter may help avoid blowout of narrow/delicate bones (e.g., a pedicle) when inserting a fastener into a bone. In some embodiments, a pilot hole may first be drilled into a narrow/delicate bone and then a fastener having a similar minor diameter in comparison to the diameter of the pilot hole may be chosen to avoid blowout when inserting the fastener into the bone.

In some embodiments, a depth of the first helical thread 110 and/or the second helical thread 120 with respect to the shaft 105 may vary along a length of the shaft 105 to define one or more major diameters of the fastener 100 and/or one or more regions along the fastener 100 may comprise a one or more continuously variable major diameters.

In some embodiments, a thickness of the shaft 105 may vary along a length of the shaft 105 to define one or more minor diameters of the fastener 100, and/or one or more regions along the fastener 100 may comprise a one or more continuously variable minor diameters. In some embodiments, a thickness/height/width/length/pitch/shape of the first helical thread 110 and/or the second helical thread 120 (or any additional helical thread) may vary along a length of the shaft 105. For example, a thickness/height/width/length/pitch/shape of the first helical thread 110 and/or the second helical thread 120 may be greater towards the tip of the fastener and thinner towards the head of the fastener (or vice versa) in either a discrete or continuously variable fashion, etc.

In some embodiments, the major and/or minor diameters may increase toward a proximal end or head of a fastener in order to increase bone compaction as the fastener is terminally inserted into the bone/tissue.

In some embodiments, a pitch of the first helical thread 110 and/or the second helical thread 120 may vary along a length of the fastener 100.

In some embodiments, the fastener 100 may include a plurality of helical threads disposed about the shaft 105. However, it will also be understood that any of the fasteners disclosed or contemplated herein may include a single helical thread disposed about the shaft of the fastener. Moreover, the fastener 100 may comprise a nested plurality of helical threads having different lengths (not shown). As one non-limiting example, the fastener 100 may include a first helical thread 110 that is longer than a second helical thread 120, such that the fastener 100 comprises dual threading along a first portion of the shaft 105 and single threading along a second portion of the shaft 105.

In some embodiments, the plurality of helical threads may include three helical threads (not shown) comprising a "triple start" or "triple lead" thread configuration (not shown).

In some embodiments, the plurality of helical threads may include four helical threads (not shown) comprising a "quadruple start" or "quadruple lead" thread configuration (not shown).

In some embodiments, the plurality of helical threads may include more than four helical threads (not shown).

In some embodiments, the fastener 100 may include first threading with any of the shapes disclosed herein oriented toward one of the proximal end and the distal end of the fastener 100 with the first threading located proximate the distal end of the fastener 100, as well as second threading with any of the shapes disclosed herein oriented toward the other one of the proximal end and the distal end of the fastener 100 with the second threading located proximate the head of the fastener 100 (not shown).

In some embodiments, the fastener 100 may include multiple threading (e.g., dual helical threading, etc.) with any of the shapes disclosed herein located proximate one of the proximal end and the distal end of the fastener 100, as well as single threading with any of the shapes disclosed herein with the second threading located proximate the other of the proximal end and the distal end of the fastener 100 (not shown).

In some embodiments, the first helical thread 110 may include a plurality of first concave undercut surfaces 131 and a plurality of first convex undercut surfaces 141.

In some embodiments, the second helical thread 120 may include a plurality of second concave undercut surfaces 132 and a plurality of second convex undercut surfaces 142.

In some embodiments, when the fastener 100 is viewed in section along a plane that intersects the longitudinal axis 103 of the shaft 105 (as shown in FIG. 1D), the plurality of first concave undercut surfaces 131 and the plurality of second convex undercut surfaces 142 may be oriented toward (i.e., point toward) the proximal end 101 of the shaft 105.

In some embodiments, the plurality of first convex undercut surfaces 141 and the plurality of second concave undercut surfaces 132 may be oriented toward (i.e., point toward) the distal end 102 of the shaft 105.

In some embodiments, at least one of the plurality of first concave undercut surfaces 131, the plurality of first convex undercut surfaces 141, the plurality of second concave undercut surfaces 132, and the plurality of second convex undercut surfaces 142 may comprise at least one substantially flat surface.

In some embodiments, when the fastener 100 is viewed in section along a plane intersecting the longitudinal axis 103 of the shaft 105, the first helical thread 110 may comprise a plurality of first bent shapes (comprising at least one surface that is angled relative to the longitudinal axis 103 of the shaft 105 and/or at least one undercut surface) with a plurality of first intermediate portions 151 that are oriented toward (i.e., point toward) the distal end 102 of the shaft 105. This may be referred to as "standard" threading, having a "standard" orientation.

In some embodiments, when the fastener 100 is viewed in section along a plane intersecting the longitudinal axis 103 of the shaft 105, the second helical thread 120 may comprise a plurality of second bent shapes (comprising at least one surface that is angled relative to the longitudinal axis 103 of the shaft 105 and/or at least one undercut surface) with a plurality of second intermediate portions 152 that are oriented toward (i.e., point toward) the proximal end 101 of the shaft 105. This may be referred to as "inverted" threading, having an "inverted" orientation.

In some embodiments, one or more helical threads may morph/transition between a standard orientation and an inverted orientation along a shaft of a fastener.

In some embodiments, at least one of the plurality of first concave undercut surfaces 131, the plurality of first convex undercut surfaces 141, the plurality of second concave undercut surfaces 132, and the plurality of second convex undercut surfaces 142 may comprise at least one curved surface.

As shown in FIG. 1D, the proximally-oriented and distally-oriented surfaces of the first helical thread 110 (i.e., the first concave undercut surfaces 131 and the first convex undercut surfaces 141 in the fastener 100 of FIG. 1D) may not have mirror symmetry relative to each other about any plane perpendicular to the longitudinal axis 103 of the fastener 100. Rather, the first concave undercut surfaces 131 and the first convex undercut surfaces 141 may be generally parallel to each other. The same may be true for the second helical thread 120, in which the second concave undercut surfaces 132 and the second convex undercut surfaces 142 do not have mirror symmetry relative to each other, but may be generally parallel to each other.

Conversely, as also shown in FIG. 1D, the proximally-oriented surfaces of the first helical thread 110 may have mirror symmetry relative to the distally-oriented surfaces of the second helical thread 120. Specifically, the first concave undercut surfaces 131 may have mirror symmetry relative to the second convex undercut surfaces 142 about a plane 170 that bisects the space between them, and lies perpendicular to the longitudinal axis 103.

Similarly, the distally-oriented surfaces of the first helical thread 110 may have mirror symmetry relative to the proximally-oriented surfaces of the second helical thread 120. Specifically, the second concave undercut surfaces 132 may have mirror symmetry relative to the first convex undercut surfaces 141 about a plane 172 that bisects the space between them, and lies perpendicular to the longitudinal axis 103.

This mirror symmetry may be present along most of the length of the first helical thread 110 and the second helical thread 120, with symmetry across different planes arranged between adjacent turns of the first helical thread 110 and the second helical thread 120 along the length of the longitudinal axis 103. Such mirror symmetry may help more effectively capture bone between the first helical thread 110 and the second helical thread 120, and may also facilitate manufacture of the fastener 100.

Figure 2:
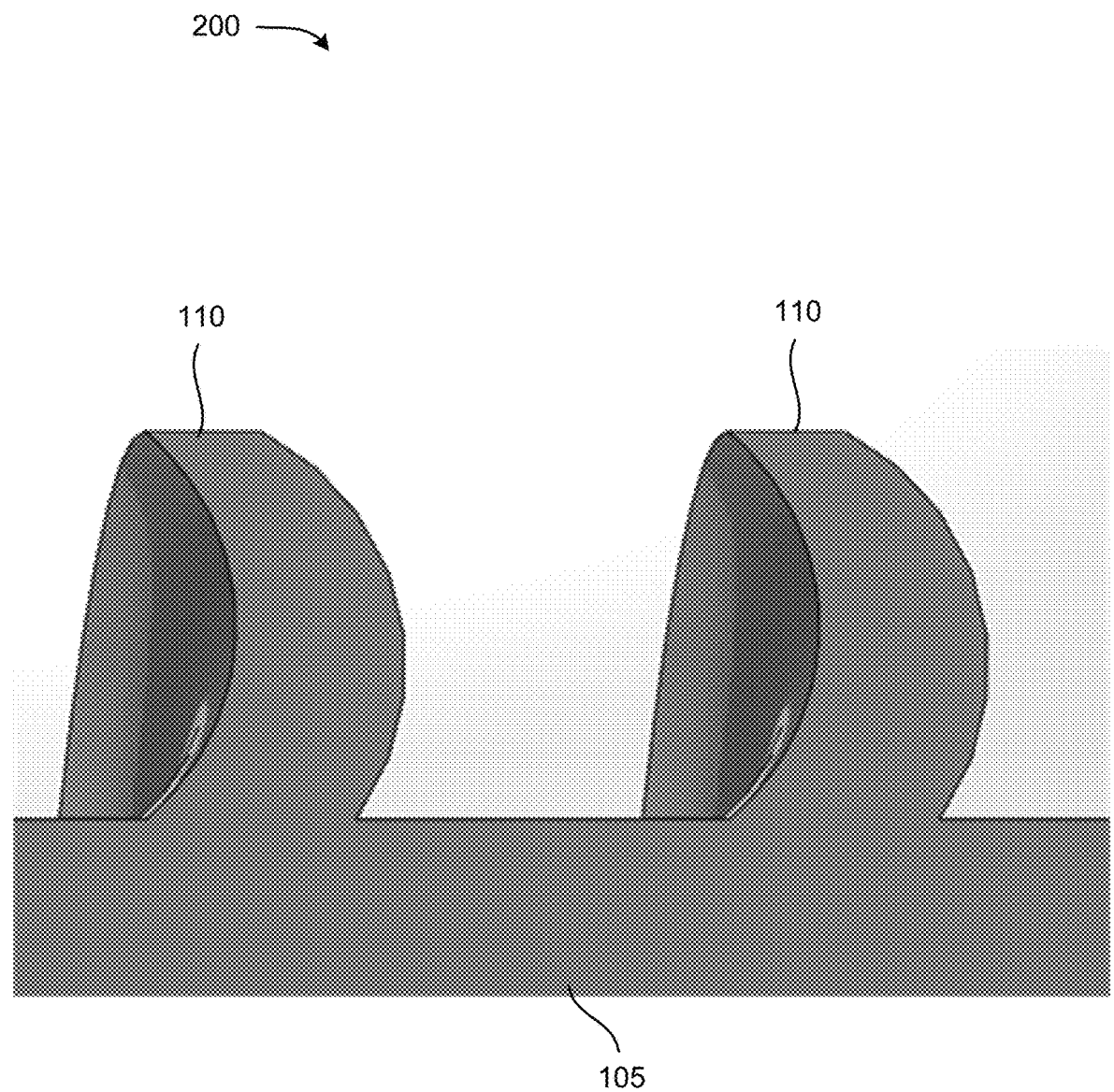
FIG. 2 illustrates a partial cross-sectional side view of a fastener comprising crescent-shaped threading.

In some embodiments, when the fastener 100 is viewed in section along a plane intersecting the longitudinal axis 103 of the shaft 105, the first helical thread 110 may include at least one partial crescent shape that is oriented toward (i.e., points toward) the distal end 102 of the shaft 105 and/or the proximal end 101 of the shaft 105. FIG. 2 illustrates a partial cross-sectional view of a fastener 200 comprising one or more partial crescent shapes, as one non-limiting example of such an embodiment.

In some embodiments (not shown), when the fastener 100 is viewed in section along a plane intersecting the longitudinal axis 103 of the shaft 105, the first helical thread 110 may include at least one partial crescent shape that is oriented toward (i.e., points toward) the distal end 102 of the shaft 105, and the second helical thread 120 may include at least one partial crescent shape that is oriented toward (i.e., points toward) the proximal end 101 of the shaft 105.

In some embodiments (not shown), the first helical thread 110 may include a first plurality of partial crescent shapes that are oriented toward (i.e., point toward) the distal end 102 of the shaft 105, and the second helical thread 120 may include a second plurality of partial crescent shapes that are oriented toward (i.e., point toward) the proximal end 101 of the shaft 105.

In some embodiments (not shown), the first plurality of partial crescent shapes and the second plurality of partial crescent shapes may be arranged in alternating succession along the shaft 105 of the fastener 100.

In some embodiments, a fastener may have only standard threads or only inverted threads. The type of threads that are desired may depend on the type and/or magnitude of loads to be applied to the fastener. For example, a fastener loaded axially away from the bone in which it is implanted may advantageously have a standard thread, while a fastener loaded axially toward the bone in which it is implanted may advantageously have an inverted thread. A fastener that may experience multi-axial loading and/or off-loading conditions may advantageously include at least one standard thread and at least one inverted thread in order to increase bone fixation and load sharing between a bone/fastener interface during multi-axial and off-loading conditions to reduce high bone strain and distribute multi-axial forces applied to the bone in a load-sharing, rather than load-bearing, configuration. Shear loads and/or bending moments may also be optimally resisted with any chosen combination of threading, threading morphology, and/or threading variations contemplated herein to optimally resist shear loads, bending moments, multi-axial loading, off-loading conditions, etc.

In some embodiments, fasteners with standard threads may be used in conjunction with fasteners with inverted threads in order to accommodate different loading patterns.

In some embodiments, a single fastener may have both standard and inverted threads, like the fastener 100. Such a combination of threads may help the fastener 100 remain in place with unknown and/or varying loading patterns.

In some embodiments, the geometry of the threading of a fastener (with standard and/or inverted threads) may be varied to suit the fastener for a particular loading scheme. For example, the number of threads, the number of thread starts, the pitch of the threading, the lead(s) of the threading, the shape(s) of the threading, any dimension(s) associated with the threading (e.g., any length(s)/width(s)/height(s) associated with the threading), the major diameter(s), the minor diameter(s), any angulation/angles associated with any surfaces of the threading, the "handedness" of the threading (e.g., right-handed vs. left-handed), etc., may be varied accordingly to suit any specific medium of installation, loading pattern, application, procedure, etc., that may be involved.

In some embodiments, the material(s) of any portion of a fastener described herein may include, but are not limited to: metals (e.g., titanium, cobalt, stainless steel, etc.), metal alloys, plastics, polymers, PEEK, UHMWPE, composites, additive particles, textured surfaces, biologics, biomaterials, bone, etc.

In some embodiments, any of the fasteners described herein may include additional features such as: self-tapping features, locking features (e.g., locking threading formed on a portion of the fastener, such as threading located on or near a head of the fastener), cannulation, any style of fastener head (or no fastener head at all), any style of torque connection interface (or no torque connection interface at all), etc.

In some embodiments, a tap may be utilized to pre-form threading in a bone according to any threading shape that is disclosed herein. In this manner, taps with any suitable shape may be utilized in conjunction with any fastener described or contemplated herein to match or substantially match the threading geometry of a given fastener.

In some embodiments, a minor diameter of the fastener may be selected to match, or substantially match, a diameter of a pilot hole that is formed in a bone to avoid bone blowout when the fastener is inserted into the pilot hole.

Additionally or alternatively, the type of threads and/or thread geometry may be varied based on the type of bone in which the fastener is to be anchored. For example, fasteners anchored in osteoporotic bone may fare better with standard or inverted threads, or when the pitch, major diameter, and/or minor diameter are increased or decreased, or when the angulation of thread surfaces is adjusted, etc.

In some embodiments, a surgical kit may include multiple fasteners with any of the different thread options described or contemplated herein. The surgeon may select the appropriate fastener(s) from the kit based on the particular loads to be applied and/or the quality of bone in which the fastener(s) are to be anchored.

Continuing with FIG. 1D, in some embodiments the first helical thread 110 may include a plurality of first undercut surfaces 111, a plurality of second undercut surfaces 112, a plurality of third undercut surfaces 113, and a plurality of fourth open surfaces 114.

In some embodiments, the second helical thread 120 may include a plurality of fifth undercut surfaces 125, a plurality of sixth undercut surfaces 126, a plurality of seventh undercut surfaces 127, and a plurality of eighth open surfaces 128.

In some embodiments one or more of the plurality of first undercut surfaces 111, the plurality of second undercut surfaces 112, the plurality of third undercut surfaces 113, the plurality of fourth open surfaces 114, the plurality of fifth undercut surfaces 125, the plurality of sixth undercut surfaces 126, the plurality of seventh undercut surfaces 127, and the plurality of eighth open surfaces 128 may comprise at least one flat or substantially flat surface.

In some embodiments, the plurality of first undercut surfaces 111, the plurality of third undercut surfaces 113, the plurality of sixth undercut surfaces 126, and the plurality of eighth open surfaces 128 may be angled towards the distal end 102 of the shaft 105.

In some embodiments, the plurality of second undercut surfaces 112, the plurality of fourth open surfaces 114, the plurality of fifth undercut surfaces 125, and the plurality of seventh undercut surfaces 127 may be angled towards the proximal end 101 of the shaft 105.

In some embodiments, when the fastener 100 is viewed in section along a plane that intersects the longitudinal axis 103 of the shaft 105 (as shown in FIG. 1D), the first helical thread 110 may include at least one chevron shape that is oriented toward (i.e., points toward) the distal end 102 of the shaft 105. Likewise, the second helical thread 120 may also include at least one chevron shape that is oriented toward (i.e., points toward) the proximal end 101 of the shaft 105.

In some embodiments, when the fastener 100 is viewed in section along a plane that intersects the longitudinal axis 103 of the shaft 105 (as shown in FIG. 1D), the first helical thread may include a first plurality of chevron shapes that are oriented toward (i.e., point toward) the distal end 102 of the shaft 105. Likewise, the second helical thread 120 may include a second plurality of chevron shapes that are oriented toward (i.e., point toward) the proximal end 101 of the shaft 105.

In some embodiments, the first plurality of chevron shapes and the second plurality of chevron shapes may be arranged in alternating succession along the shaft 105 of the fastener 100, (e.g., see FIG. 1D).

In some embodiments, a plurality of first interlocking spaces 161 and a plurality of second interlocking spaces 162 may be formed between the first helical thread 110 and the second helical thread 120 along the shaft 105 of the fastener 100.

In some embodiments, the plurality of first interlocking spaces 161 may be formed intermediate the first concave undercut surfaces 131 and the second concave undercut surfaces 132.

In some embodiments, the plurality of second interlocking spaces 162 may be formed intermediate the first convex undercut surfaces 141 and the second convex undercut surfaces 142.

In some embodiments, the plurality of first interlocking spaces 161 may be larger in size than the plurality of second interlocking spaces.

In some embodiments, the plurality of first interlocking spaces 161 and the plurality of second interlocking spaces 162 may be shaped and/or configured to interlock with bone/other tissues received therein to increase fixation of the fastener 100 within the bone/other tissues and provide additional resistance against multi-axial forces that may be applied to the fastener 100 and/or the bone/other tissues.

In some embodiments, the plurality of second undercut surfaces 112 and the plurality of sixth undercut surfaces 126 may be angled toward each other to trap bone/other tissues within the plurality of first interlocking spaces 161 in order to increase fixation and resistance against multi-axial forces.

In some embodiments, the plurality of third undercut surfaces 113 and the plurality of seventh undercut surfaces 127 may be angled toward each other to trap bone/other tissues within the plurality of second interlocking spaces 162 in order to increase fixation and resistance against multi-axial forces.

In some embodiments, the plurality of first undercut surfaces 111 and the plurality of fifth undercut surfaces 125 may each form an angle $\alpha$ with respect to the longitudinal axis 103 of the shaft 105, as shown in FIG. 1D.

In some embodiments, the angle $\alpha$ may be greater than 90 degrees.

In some embodiments, the plurality of second undercut surfaces 112 and the plurality of sixth undercut surfaces 126 may each form an angle $\beta$ with respect to the longitudinal axis 103 of the shaft 105.

In some embodiments, the angle $\beta$ may be less than 90 degrees.

In some embodiments, the plurality of third undercut surfaces 113 and the plurality of seventh undercut surfaces 127 may each form an angle $\theta$ with respect to the longitudinal axis 103 of the shaft 105.

In some embodiments, the angle $\theta$ may be approximately 90 degrees.

In some embodiments, the angle $\theta$ may be greater than 90 degrees.

Figure 3A:
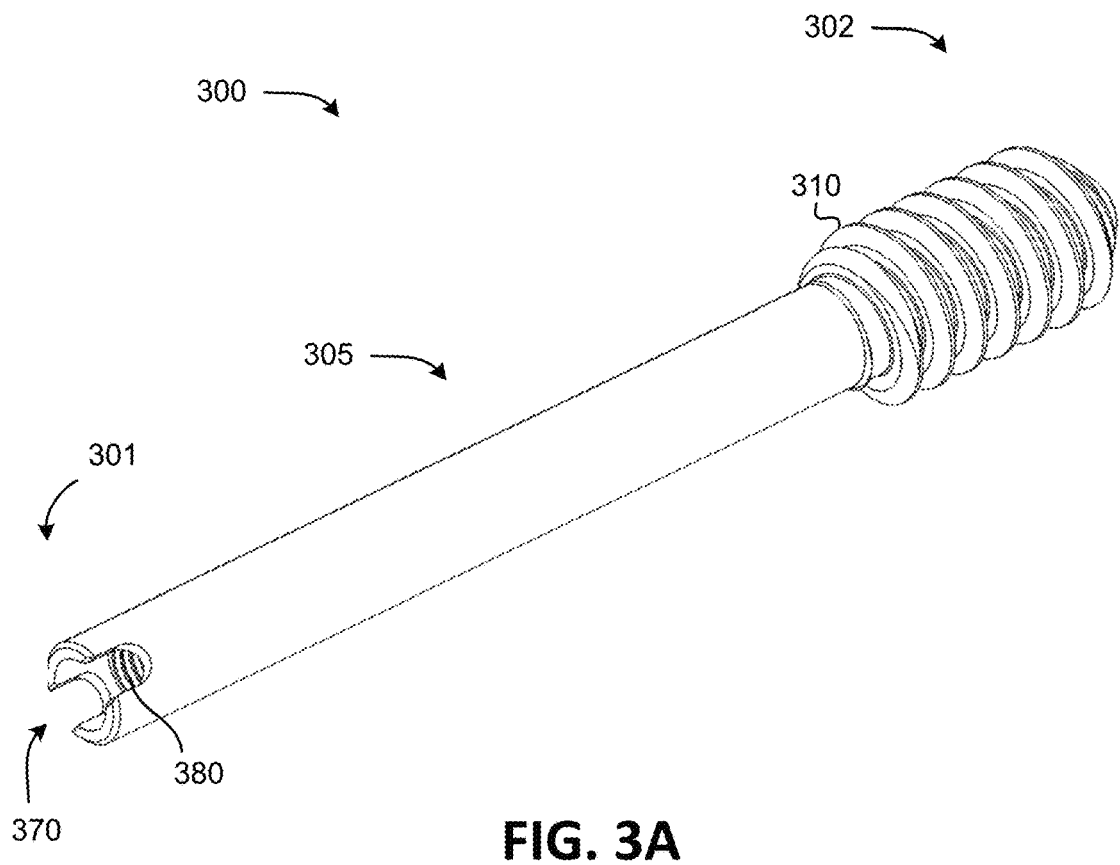
FIG. 3A illustrates a rear perspective view of a femoral fastener, according to an embodiment of the present disclosure.
Figure 3B:
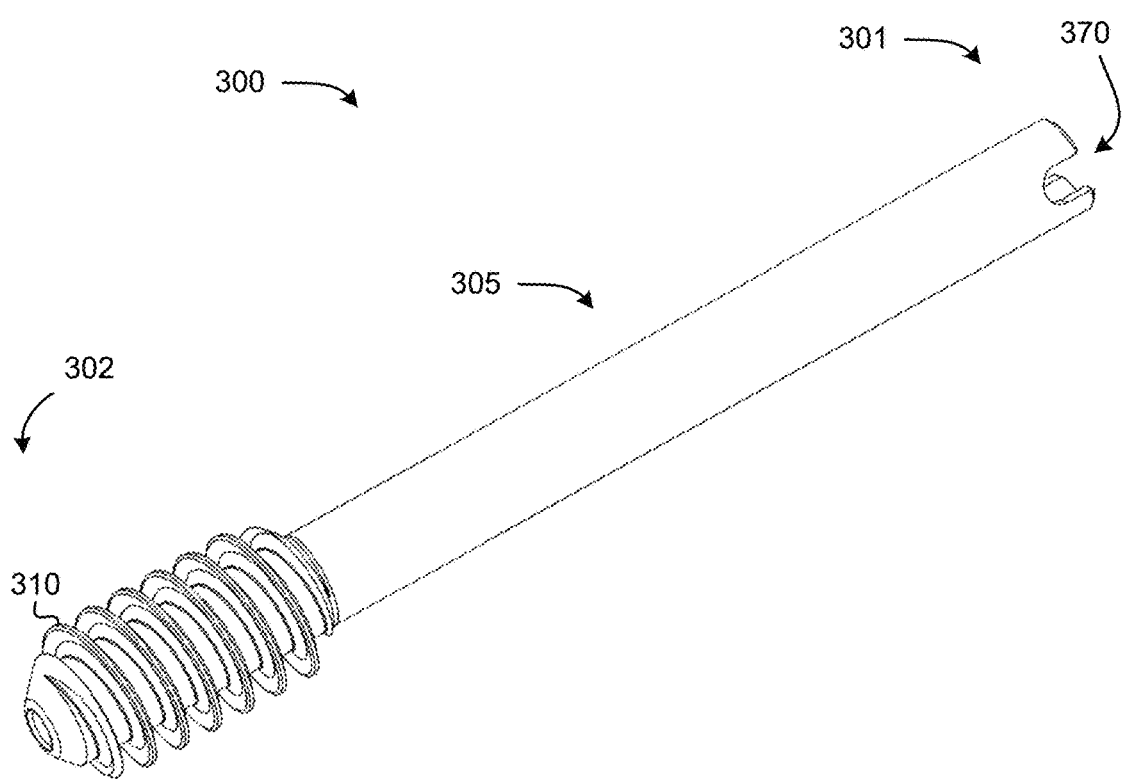
FIG. 3B illustrates a front perspective view of the femoral fastener of FIG. 3A.
Figure 3C:
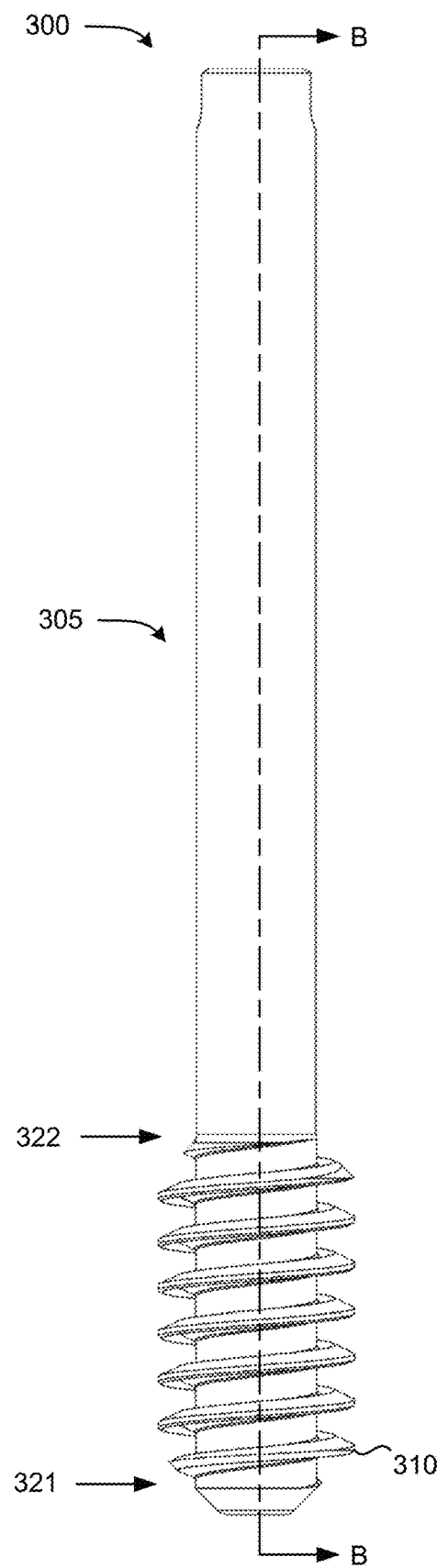
FIG. 3C illustrates a side view of the femoral fastener of FIG. 3A.
Figure 3D:
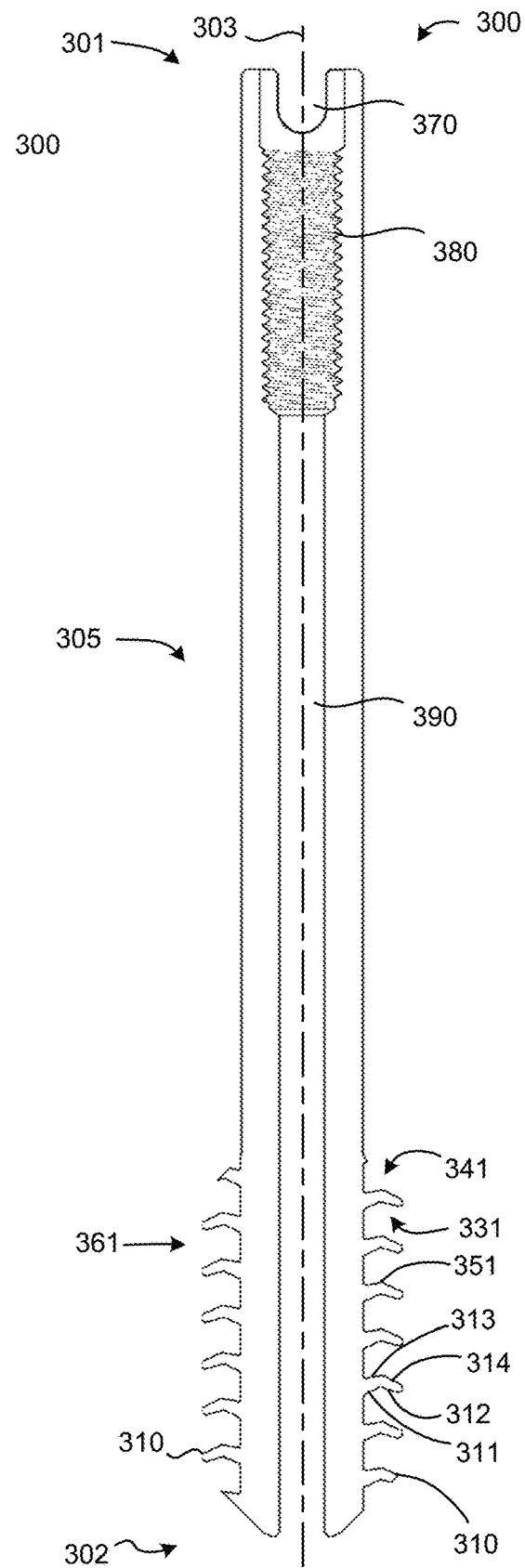
FIG. 3D illustrates a cross-sectional side view of the fastener shown in FIG. 3C, taken along the line B-B.

FIGS. 3A-D illustrate various views of a femoral fixation device or femoral fastener 300, according to another example of the present disclosure. Specifically, FIG. 3A is a rear perspective view of the femoral fastener 300, FIG. 3B is a front perspective view of the femoral fastener 300, FIG. 3C is a side view of the femoral fastener 300, and FIG. 3D is a cross-sectional side view of the femoral fastener 300 taken along the line B-B in FIG. 3C.

In general, the femoral fastener 300 may include a shaft 305 having a proximal end 301, a distal end 302, and a longitudinal axis 303, as well as a helical thread 310 disposed about at least a portion of the shaft 305.

In some embodiments, the shaft 305 of the femoral fastener 300 may be cannulated with a through bore 390.

In some embodiments, the through bore 390 may include an internal thread 380 formed along at least a portion of a length of the through bore 390.

In some embodiments, the internal thread 380 may be located toward the proximal end 301 of the shaft 305.

In some embodiments, the proximal end 301 of the femoral fastener 300 may comprise a headless fastener design having an at least partially cylindrical shape.

In some embodiments, the proximal end 301 of the femoral fastener 300 may include one or more recesses 370 which may extend along the shaft from the proximal end 301 of the shaft 305 toward the distal end 302 of the shaft 305.

In some embodiments, the one or more recesses 370 may be shaped and configured to couple with an inserter tool to form a torque connection interface that may facilitate insertion of the femoral fastener 300, as will be discussed in more detail below.

In some embodiments, the femoral fastener 300 may include one or more self-tapping or bone cutting features formed in a distal portion of the femoral fastener 300 (not shown).

In some embodiments, the helical thread 310 may be disposed about the shaft 305 along the longitudinal axis 303 between a first location 321 and a second location 322 along the shaft 305.

Although the femoral fastener 300 shown in FIGS. 3A-3D illustrates a single helical thread design, it will be understood that the femoral fastener 300 may include any number of threads and/or any number of thread characteristics, shapes, or configurations that are described or contemplated herein, in any combination. For example, the femoral fastener 300 may include a "dual start" or "dual lead" thread configuration comprising a first helical thread and a second helical thread as previously described herein, etc.

In some embodiments, a depth of the helical thread 310 with respect to the shaft 305 may define a major diameter vs. a minor diameter of the shaft 305 alone.

In some embodiments, the major diameter, the minor diameter, and/or a pitch of the helical thread 310 may be constant or substantially constant along a length of the femoral fastener 300.

In some embodiments, the helical thread 310 may include one or more concave undercut surfaces 331 and/or one or more convex undercut surfaces 341.

In some embodiments, the one or more concave undercut surfaces 331 may be angled towards one of the proximal end 301 and the distal end 302 of the shaft 305.

In some embodiments, the one or more convex undercut surfaces 341 may be angled towards the other one of the proximal end 301 and the distal end 302 of the shaft 305.

In some embodiments, the one or more concave undercut surfaces 331 may be angled towards the proximal end 301 of the shaft 305 and the one or more convex undercut surfaces 341 may be angled towards the distal end 302 of the shaft 305.

In some embodiments, the one or more concave undercut surfaces 331 and/or the one or more convex undercut surfaces 341 may include a plurality of flat surfaces that are angled relative to each other.

In some embodiments, the helical thread 310 may include one or more first undercut surfaces 311 and one or more second undercut surfaces 312.

In some embodiments, the one or more first undercut surfaces 311 may be angled toward the proximal end 301 of the shaft 305 and one or more second undercut surfaces 312 may be angled toward the distal end 302 of the shaft 305.

In some embodiments, the helical thread 310 may also include one or more third undercut surfaces 313 and one or more fourth open surfaces 314. However, it will be understood that in other embodiments the one or more third undercut surfaces 313 and the one or more fourth open surfaces 314 may be replaced with any other shaped surface or surfaces (e.g., any buttress type thread shape, any flat surface that is angled toward or away from the one or more concave undercut surfaces 331, or angled 90 degrees with respect thereto, any curved surface that is generally oriented toward or away from the one or more concave undercut surfaces, etc.) without departing from the spirit or scope of the present disclosure.

In some embodiments, when the femoral fastener 300 is viewed in section along a plane intersecting the longitudinal axis 303 of the shaft 305, the helical thread 310 may include at least one chevron shape oriented toward the proximal end 301 of the shaft 305.

In some embodiments, when the femoral fastener 300 is viewed in section along a plane intersecting the longitudinal axis 303 of the shaft 305, the helical thread 310 may include a plurality of chevron shapes oriented toward the proximal end 301 of the shaft 305.

In some embodiments, when the femoral fastener 300 is viewed in section along a plane intersecting the longitudinal axis 303 of the shaft 305, the helical thread 310 may include at least one partial crescent shape oriented toward the proximal end 301 or the distal end 302 of the shaft 305.

In some embodiments, when the femoral fastener 300 is viewed in section along a plane intersecting the longitudinal axis 303 of the shaft 305, the helical thread 310 may include a plurality of partial crescent shapes oriented toward the proximal end 301 or the distal end 302 of the shaft 305.

In some embodiments, when the femoral fastener 300 is implanted within a neck 710 and a head 720 of a femoral bone or femur 700, the first location 321, the second location 322, and the helical thread 310 extending therebetween may be disposed within the head 720 of the femur 700.

In some embodiments, when the femoral fastener 300 is implanted within a neck 710 and a head 720 of a femur 700, at least one of: the one or more concave undercut surfaces 331, the one or more convex undercut surfaces 341, the one or more first undercut surfaces 311, the one or more second undercut surfaces 312, the one or more third undercut surfaces 313, and/or the one or more fourth open surfaces 314 may be configured to transmit at least one force from the head 720 of the femur 700 to the neck 710 (or other portion) of the femur 700. In this manner, the unique shape and configuration of the helical thread 310 can help mitigate or prevent loosening of the femoral fastener 300 over time due to multi-axial forces and off-axis loading scenarios that may be applied to the femoral fastener 300.

In some embodiments, one or more interlocking spaces 361 may be formed between adjacent thread portions of the helical thread 310 along the shaft 305 of the femoral fastener 300.

In some embodiments, the one or more interlocking spaces 361 may be shaped and/or configured to interlock with bone/other tissues received therein to increase fixation of the femoral fastener 300 within the bone/other tissues and provide additional resistance against multi-axial forces that may be applied to the femoral fastener 300 and/or the bone/other tissues.

In some embodiments, when the femoral fastener 300 is viewed in section along a plane intersecting the longitudinal axis 303 of the shaft 305, the helical thread 310 may include one or more bent shapes (comprising at least one surface that is angled relative to the longitudinal axis 303 of the shaft 305 and/or at least one undercut surface) with one or more intermediate portions 351 that are oriented toward (i.e., point toward) one of the proximal end 301 and the distal end 302 of the shaft 305.

In some embodiments, at least one of: the one or more concave undercut surfaces 331, the one or more convex undercut surfaces 341, the one or more first undercut surfaces 311, the one or more second undercut surfaces 312, the one or more third undercut surfaces 313, and/or the one or more fourth open surfaces 314 may comprise at least one substantially flat surface.

In some embodiments, at least one of: the one or more concave undercut surfaces 331, the one or more convex undercut surfaces 341, the one or more first undercut surfaces 311, the one or more second undercut surfaces 312, the one or more third undercut surfaces 313, and/or the one or more fourth open surfaces 314 may comprise at least one curved surface.

Figure 4C:
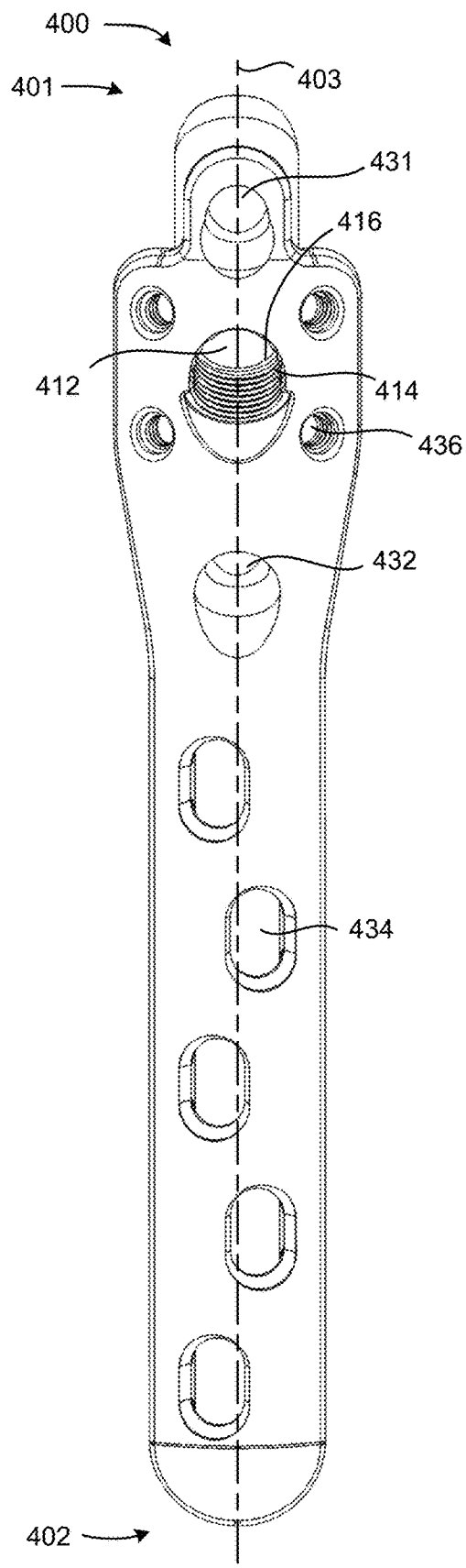
FIG. 4C illustrates a front view of the femoral support member of FIG. 4A.
Figure 4D:
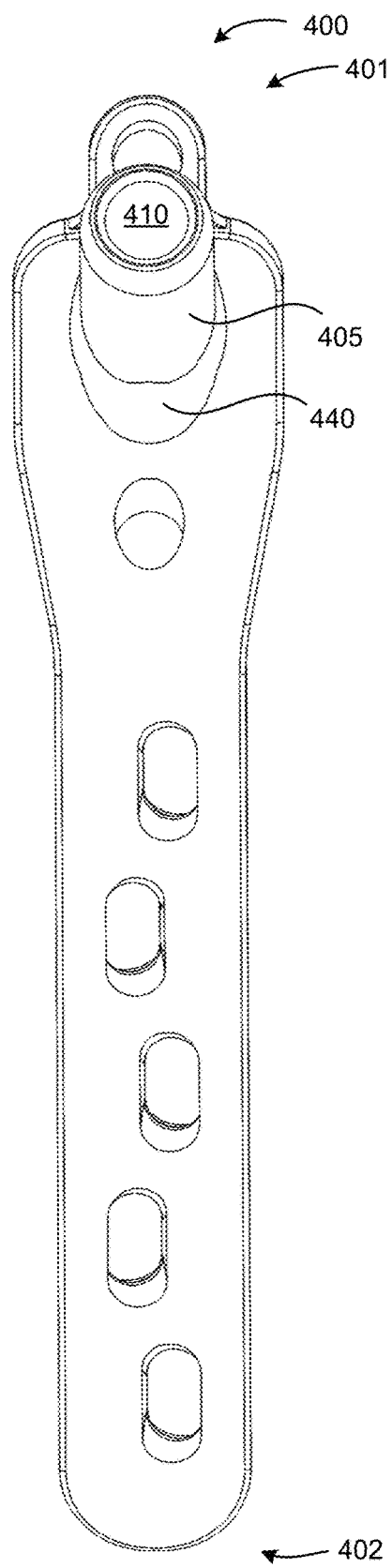
FIG. 4D illustrates a rear view of the femoral support member of FIG. 4A.

FIGS. 4A-D illustrate various views of a femoral support member 400, according to an example of the present disclosure. Specifically, FIG. 4A is a perspective side view of the femoral support member 400, FIG. 4B is another perspective side view of the femoral support member 400, FIG. 4C is a front view of the femoral support member 400, and FIG. 4D is a rear view of the femoral support member 400.

In general, the femoral support member 400 may include an elongate body having a proximal end 401, a distal end 402, a longitudinal axis 403, and a barrel 405.

In some embodiments, the femoral support member 400 may comprise a bone plate.

In some embodiments, the femoral support member 400 may comprise an intramedullary nail (not shown).

In some embodiments, the femoral support member 400 may include one or more bone plate apertures 434, one or more inferior support apertures 432, one or more superior support apertures 431, and/or one or more extension plate apertures 436.

In some embodiments, the barrel 405 may include a passageway 410 formed therethrough having a first opening 411 and a second opening 412 opposite the first opening 411.

In some embodiments, the passageway 410 may also include an internal thread 414 and a barrel shoulder 416 located adjacent the internal thread 414.

Figure 7:
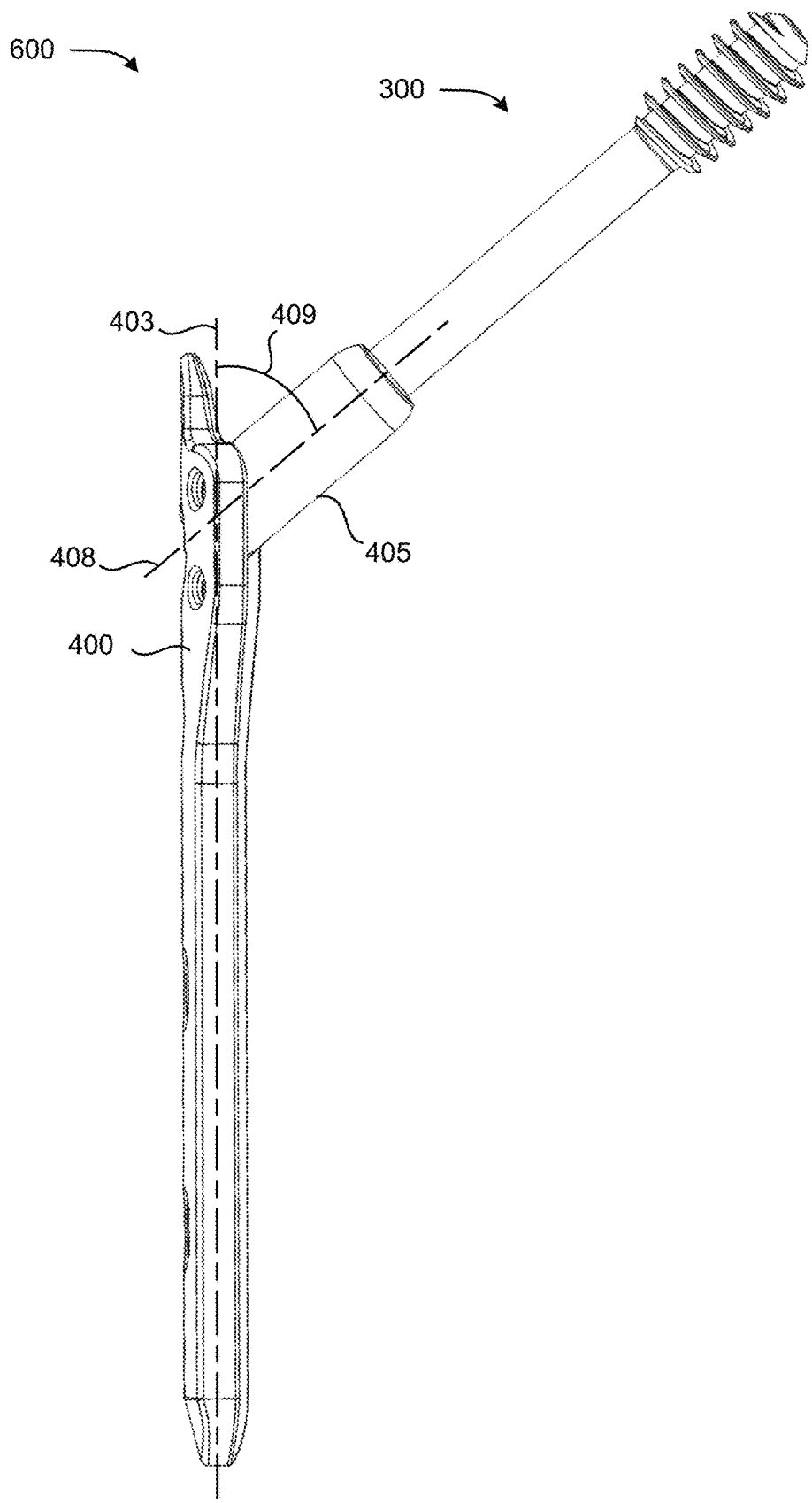
FIG. 7 illustrates a side view of the femoral fixation assembly of FIG. 6, after it has been assembled.

In some embodiments, the barrel 405 and/or the passageway 410 may be formed through the femoral support member 400 with a longitudinal axis 408 at an angle 409 with respect to the longitudinal axis 403 of the femoral support member 400, as shown in FIG. 7.

In some embodiments, the angle 409 of the barrel 405 and/or the passageway 410 with respect to the longitudinal axis 403 of the femoral support member 400 may be an acute angle. However, it will also be understood that in some embodiments the angle 409 may be a right angle and/or an obtuse angle.

Figure 5A:
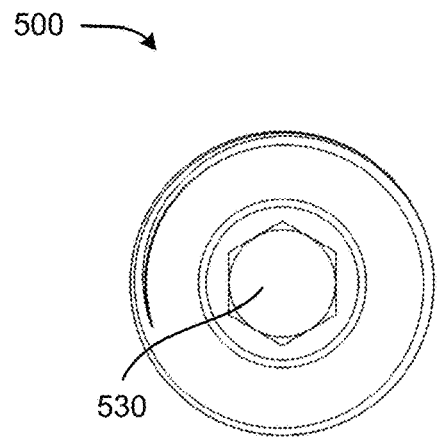
FIG. 5A illustrates a front view of a stop member, according to an embodiment of the present disclosure.
Figure 5D:
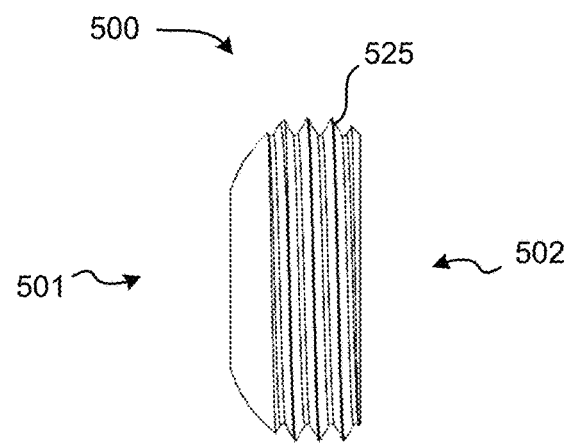
FIG. 5D illustrates a side view of the stop member of FIG. 5A.
Figure 5B:
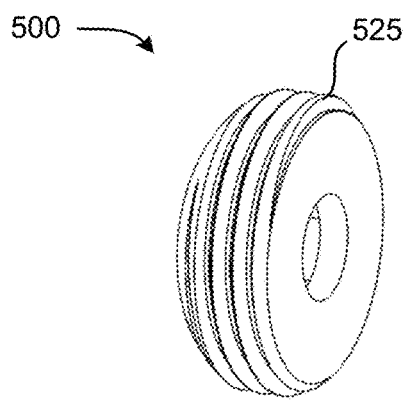
FIG. 5B illustrates a rear perspective view of the stop member of FIG. 5A.
Figure 5E:
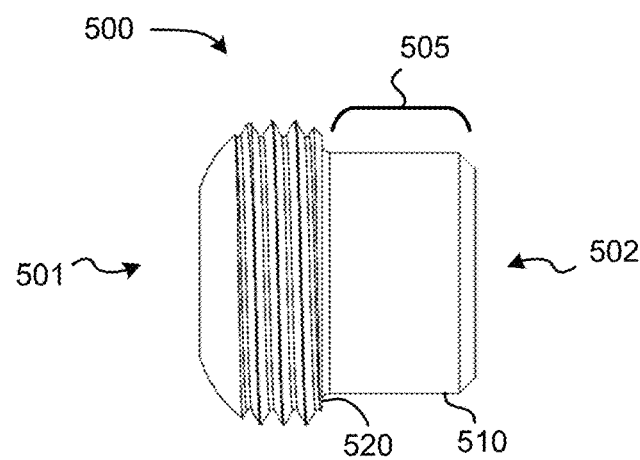
FIG. 5E illustrates a side view of the stop member of FIG. 5A with a stop member projection.
Figure 5C:
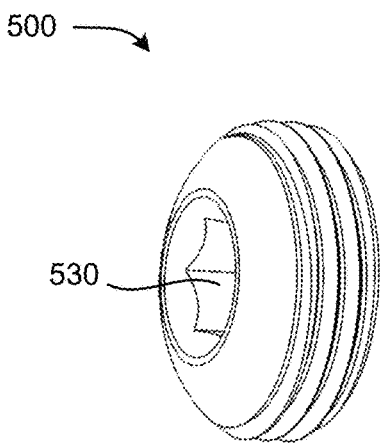
FIG. 5C illustrates a front perspective view of the stop member of FIG. 5A.
Figure 5F:
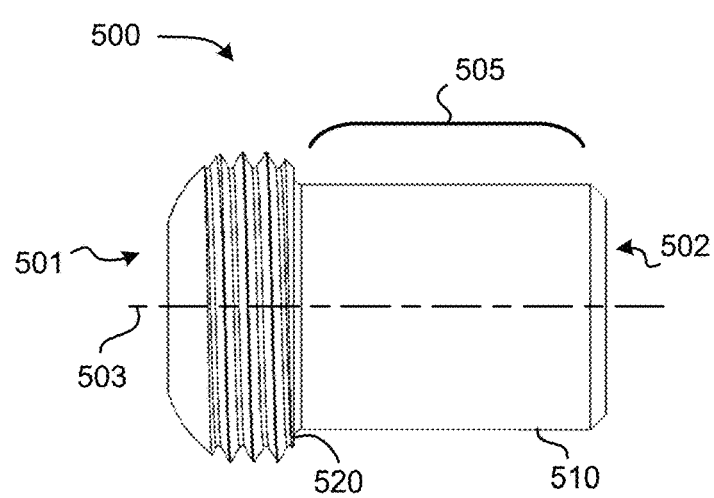
FIG. 5F illustrates a side view of the stop member of FIG. 5A with another stop member projection.

FIGS. 5A-F illustrate various views of a stop member 500, according to an example of the present disclosure. Specifically, FIG. 5A is a front view of the stop member 500, FIG. 5B is a rear perspective view of the stop member 500, FIG. 5C is a front perspective view of the stop member 500, FIG. 5D is a side view of the stop member 500, and FIGS. 5E and 5F are side views of the stop member 500 including a stop member projection 510 having a preselected length 505.

In general, the stop member 500 may include a proximal end 501, a distal end 502, and a longitudinal axis 503.

In some embodiments, the stop member 500 may include a torque connection interface 530. In some embodiments, the torque connection interface 530 may comprise a hexagonal shape. However, it will be understood that the torque connection interface 530 may comprise any shape suitable for receiving a torque force from a driver tool, as will be discussed in more detail below.

In some embodiments, the stop member 500 may include an external thread 525.

In some embodiments, the stop member 500 may include a stop member shoulder intermediate the external thread 525 and the stop member projection 510.

In some embodiments, the preselected length 505 of the stop member projection 510 may be zero.

In some embodiments, the preselected length 505 of the stop member projection 510 may be greater than zero.

In some embodiments, the preselected length 505 of the stop member projection 510 may be 3*mm*, 5*mm*, 10*mm*, etc., as some non-limiting examples of a preselected length 505 that is greater than zero. However, it will be understood that any length greater than or equal to zero may be utilized for the preselected length 505 of the stop member projection 510.

Figure 6:
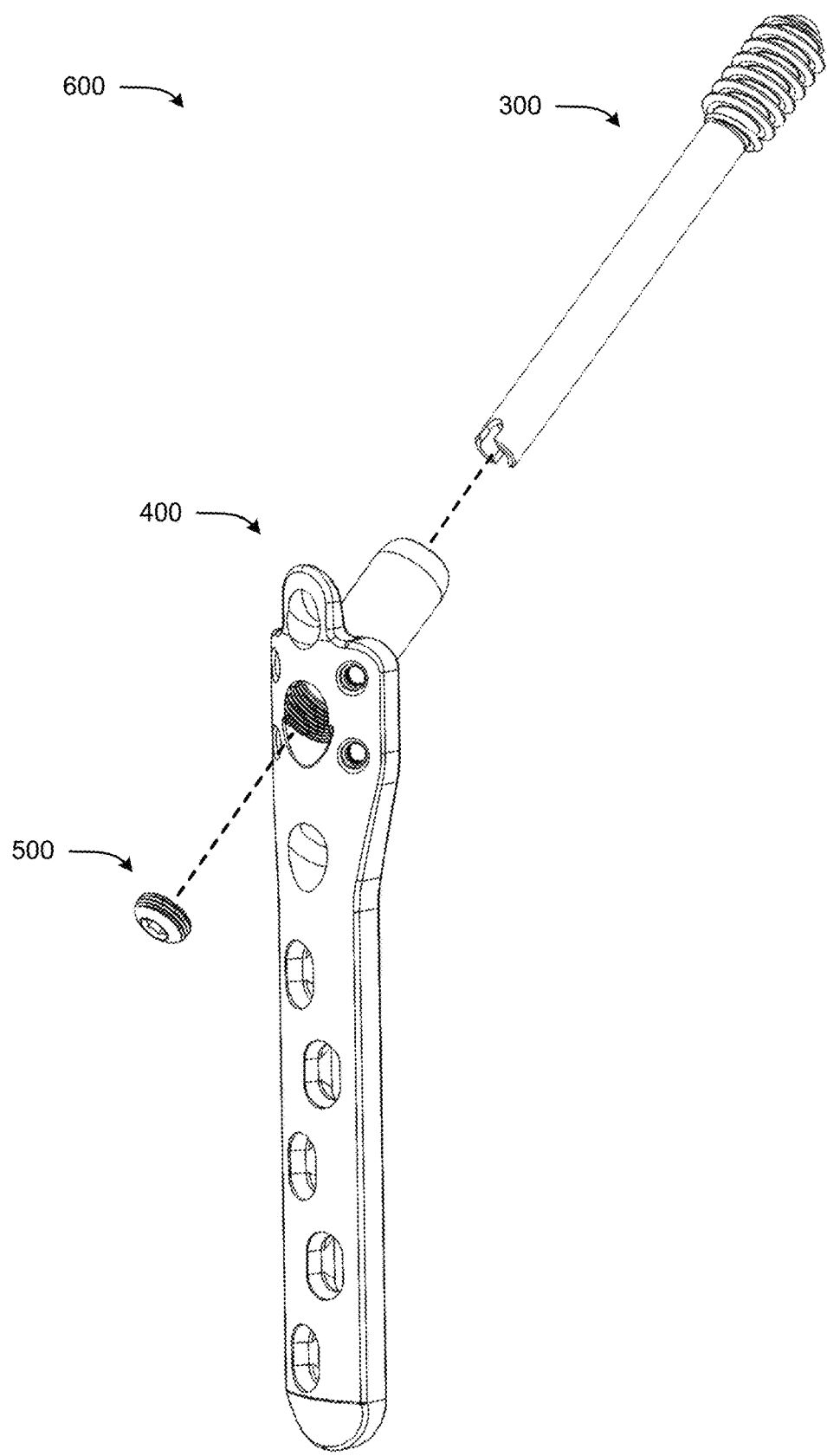
FIG. 6 illustrates an exploded view of a femoral fixation assembly, according to an embodiment of the present disclosure.
Figure 8:
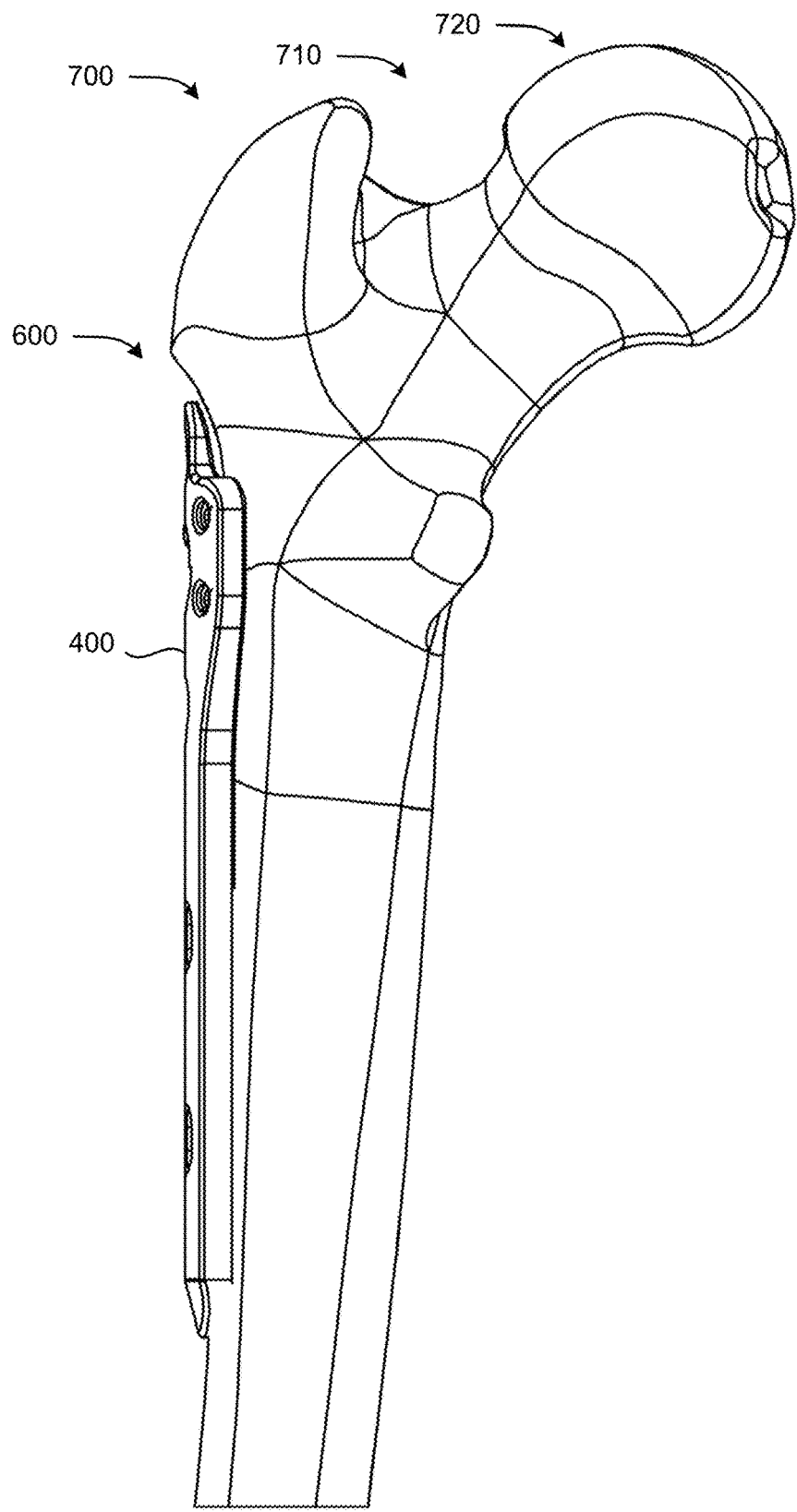
FIG. 8 illustrates a side view of the femoral fixation assembly of FIG. 6 implanted in a femur.
Figure 9:
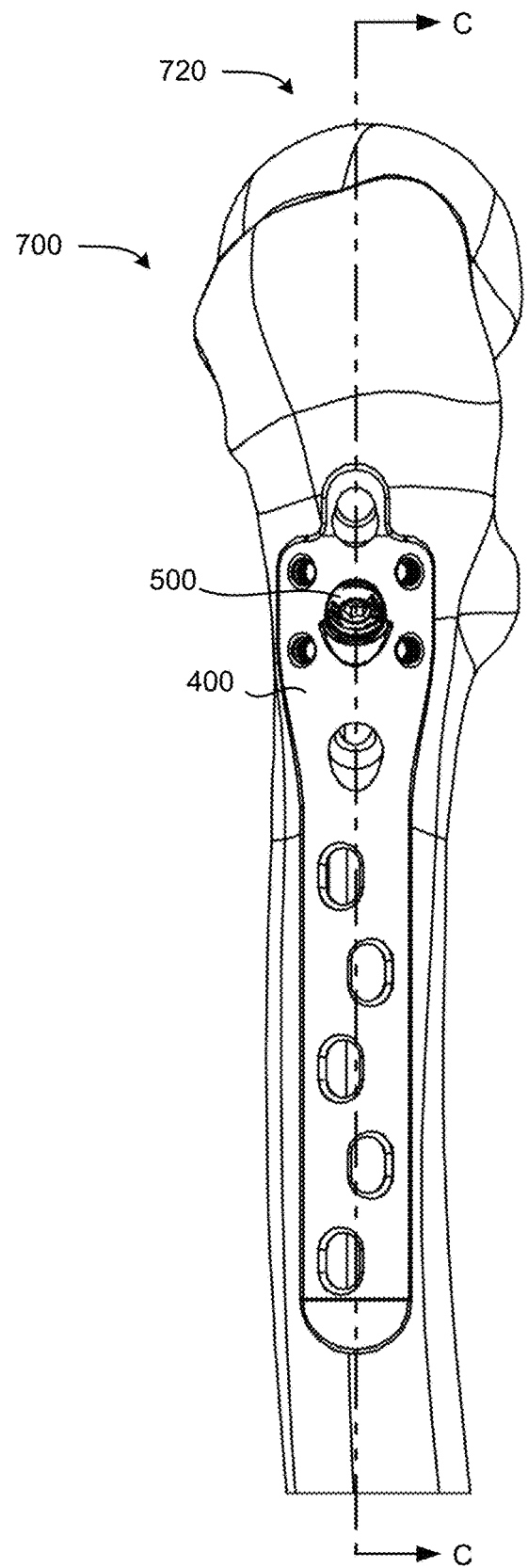
FIG. 9 illustrates a front view of the femoral fixation assembly and femur shown in FIG. 8.
Figure 10:
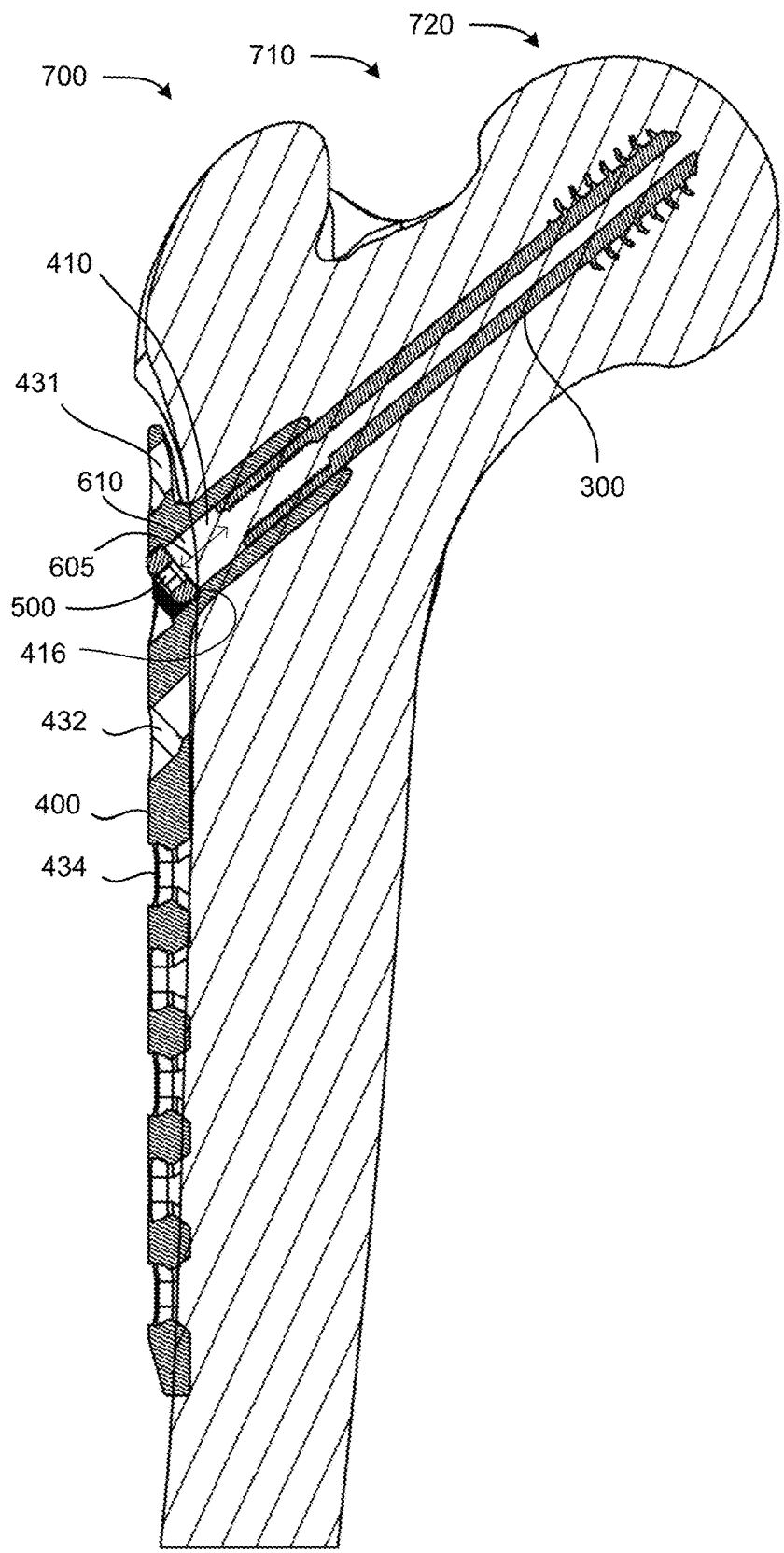
FIG. 10 illustrates cross-sectional side view of the femoral fixation assembly and femur shown in FIG. 9, taken along the line C-C.

FIGS. 6-10 illustrate various views of a femoral fixation assembly 600 comprising the femoral support member 400, the femoral fastener 300, and the stop member 500, according to an embodiment of the present disclosure. Specifically, FIG. 6 illustrates an exploded view of the femoral fixation assembly 600; FIG. 7 illustrates a side view of the femoral fixation assembly 600 after assembly; FIG. 8 illustrates a side view of the femoral fixation assembly 600 implanted into a femur 700; FIG. 9 illustrates a front view of the femoral fixation assembly 600 and femur 700 of FIG. 8; and FIG. 10 illustrates cross-sectional side view of the femoral fixation assembly 600 and femur 700 of FIG. 9 taken along the line C-C.

With reference to FIG. 10, when the femoral fastener 300 is implanted within the neck 710 and the head 720 of the femur 700, and the femoral support member 400 is oriented with respect to a longitudinal axis of the femoral bone, at least a portion of the shaft 305 of the femoral fastener 300 may be slidingly received within the passageway 410 of the barrel 405 through the first opening 411 of the passageway 410.

In this manner, the femoral fastener 300 may be allowed to slide further into the passageway 410 of the barrel 405 as the femur 700 collapses due to the bone remodeling process, the healing process, continued use of the femur over time, etc.

However, it may be desirable to limit the amount of collapse that the femur 700 may undergo. Accordingly, in some embodiments, the stop member 500 may be inserted into the passageway 410 in order to set a predetermined limit to the amount of collapse that the femur 700 may be permitted to undergo.

In some embodiments, at least a portion of the stop member 500 may be received within the passageway 410 through the second opening 412.

In some embodiments, the stop member 500 may be inserted into the passageway 410 and coupled thereto by engaging the external thread 525 of the stop member 500 with the internal thread 380 of the femoral fastener 300.

In some embodiments, a stop member shoulder 520 of the stop member 500 may be configured to abut against a barrel shoulder 416 of the passageway 410 when the stop member 500 has been fully inserted into the passageway 410.

In some embodiments, a space 610 having a predetermined length 605 may be formed within the passageway 410 between the distal end 502 of the stop member 500 and the proximal end 301 of the shaft 305 based on the preselected length 505 of the stop member projection 510. The predetermined length 605 of the space 610 may define the amount of collapse that the femur 700 may be permitted to undergo.

In some embodiments, the preselected length 505 of the stop member projection 510 may be selected such that the predetermined length 605 of the space 610 within the passageway 410 may be zero. In these embodiments, the distal end 502 of the stop member 500 may abut against the proximal end 301 of the femoral fastener 300 to prevent collapse.

In some embodiments, the preselected length 505 of the stop member projection 510 may be selected such that the predetermined length 605 of the space 610 within the passageway 410 may be greater than zero. In these embodiments, the predetermined length 605 of the space 610 in the passageway 410 may define the amount of collapse that the femur 700 may be permitted to undergo.

FIGS. 11-35 illustrate various views of a surgical procedure that may be utilized to install the femoral fixation assembly 600 into a femur 700.

Figure 11:
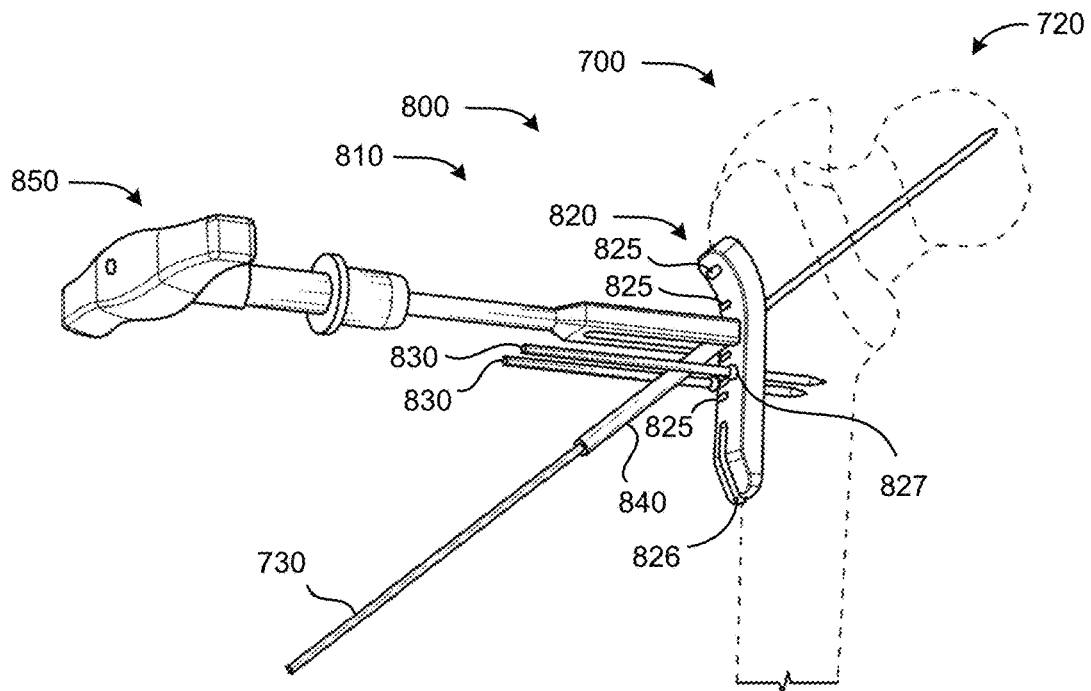
FIG. 11 illustrates a perspective side view of a guide pin inserter assembly adjacent a femur, according to an embodiment of the present disclosure.
Figure 12:
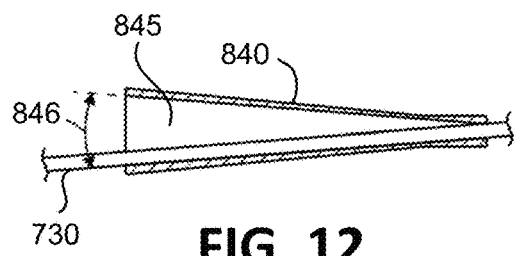
FIG. 12 illustrates cross-sectional side view of a guide pin insert, according to an embodiment of the present disclosure.

FIG. 11 illustrates a perspective side view of a guide pin inserter assembly 800 placed adjacent a femur 700, according to an embodiment of the present disclosure.

The guide pin inserter assembly 800 may generally include a handle 850, a side plate positioner 810 coupled to the handle 850, a side plate guide 820 coupled to the side plate positioner 810, and a guide pin insert 840 coupled to the side plate guide 820.

In some embodiments, one or more of the handle 850, the side plate positioner 810, the side plate guide 820, and/or the guide pin insert 840 may each be removably couplable with each other.

In some embodiments, one or more of the handle 850, the side plate positioner 810, the side plate guide 820, and/or the guide pin insert 840 may be integrally formed with each other. For example, in some embodiments the side plate positioner 810 and the side plate guide 820 may be integrally formed with each other.

The side plate guide 820 may be placed against the lateral side of the femur 700 by manipulating the handle 850 to orient the side plate guide 820 with respect to a longitudinal axis of the femur. Once the side plate guide 820 has been properly located adjacent the lateral side of the femur 700, one or more placement pins 830 may be inserted through apertures 827 formed in the side plate guide 820 to pin the side plate guide 820 to the femur 700.

Once the side plate guide 820 has been pinned to the femur 700 at a desired location, the guide pin insert 840 may be coupled to the side plate guide 820 by inserting a distal end of the guide pin insert 840 into one of the locating slots 825 of the side plate guide 820, depending on a desired superior/inferior location and/or trajectory for the guide pin 730.

In some embodiments, an interior space 845 of the guide pin insert 840 may be substantially straight and/or cylindrical in shape in order to direct the guide pin 730 along a single trajectory into the head 720 of the femur 700.

In some embodiments, the interior space 845 of the guide pin insert 840 may be flared and/or somewhat conical in shape in order to allow the surgeon some degree of latitude to choose a trajectory for the guide pin 730 into the head 720 of the femur 700.

In some embodiments, the interior space 845 of the guide pin insert 840 may include an angle 846 that allows the trajectory of the guide pin 730 to be varied in at least an anterior-posterior direction.

In some embodiments, the angle 846 may be about 9 degrees, as one non-limiting example. However, it will be understood that the interior space 845 may comprise any angle.

Figure 35:
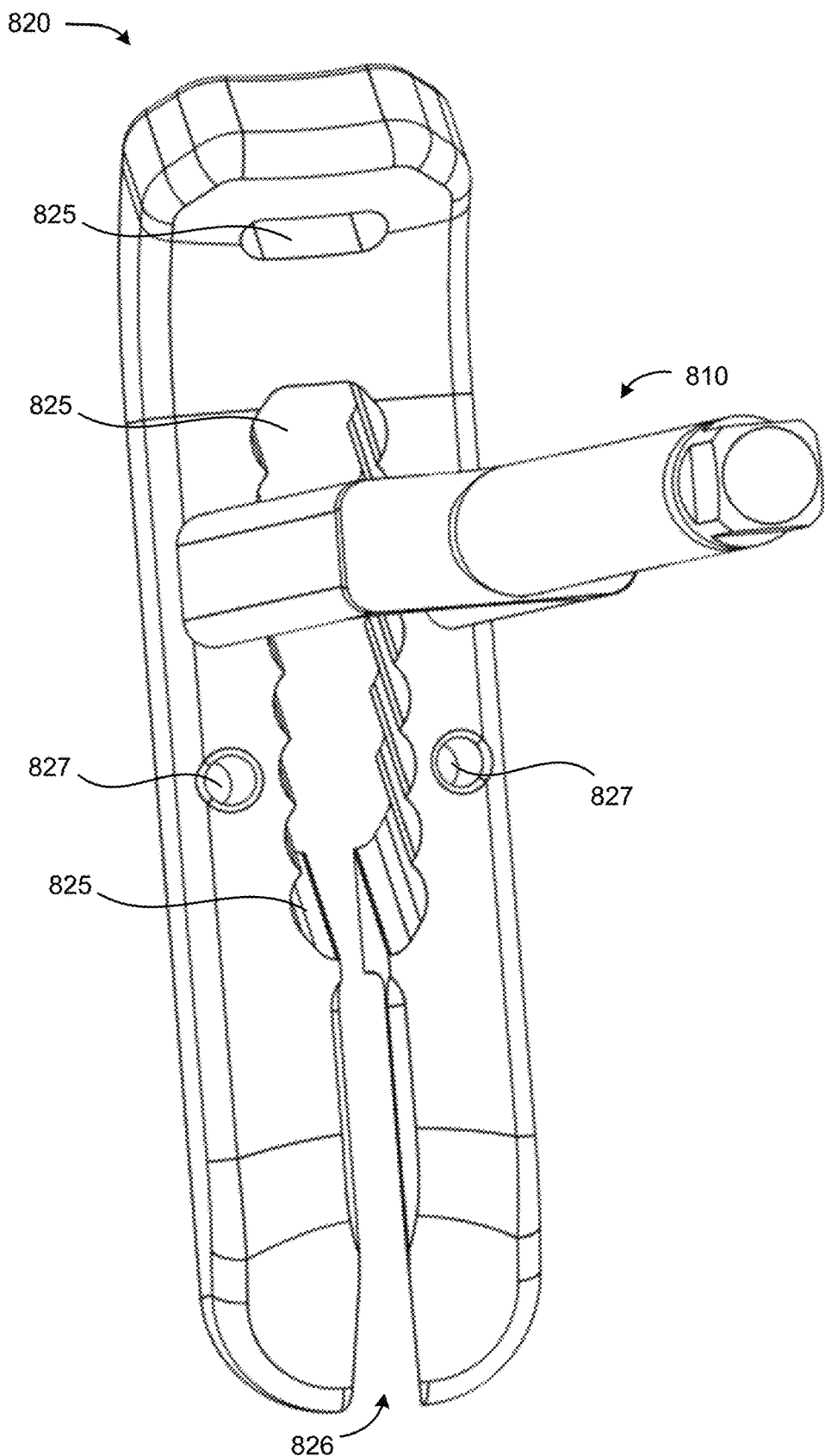
FIG. 35 illustrates a perspective front view of a side plate guide, according to another embodiment of the present disclosure.

In some embodiments, once the guide pin 730 has been properly placed within the head 720 of the femur 700, the guide pin inserter assembly 800 may be removed from the femur without disturbing the guide pin 730 by sliding the side plate guide 820 superiorly. In these embodiments, the guide pin insert 840 may be removed from the guide pin 730, and then the side plate guide 820 may be moved superiorly to allow the guide pin 730 to exit the side plate guide 820 inferiorly through the removal slot 826 that is formed in the side plate guide 820. In these embodiments, the removal slot 826 may extend further superiorly (than what is illustrated in FIG. 11) in order to provide a channel through which the guide pin 730 may exit the side plate guide 820 inferiorly as the side plate guide 820 is moved superiorly. For example, FIG. 35 illustrates a side plate guide 820 comprising a removal slot 826 extending superiorly to connect with the one or more locating slots 825. In this manner, the guide pin 730 may be allowed to exit the side plate guide 820 inferiorly through the removal slot 826 as the side plate guide 820 is moved superiorly.

Figure 13:
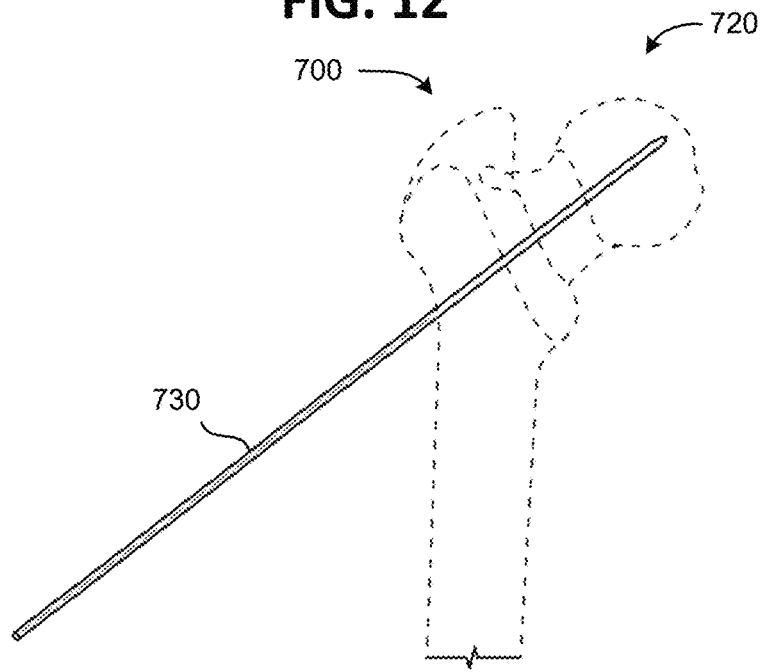
FIG. 13 illustrates a side view of a guide pin inserted into a femur.

FIG. 13 illustrates a side view of a guide pin 730 located in the femur 700 after the guide pin inserter assembly 800 has been removed.

Figure 14:
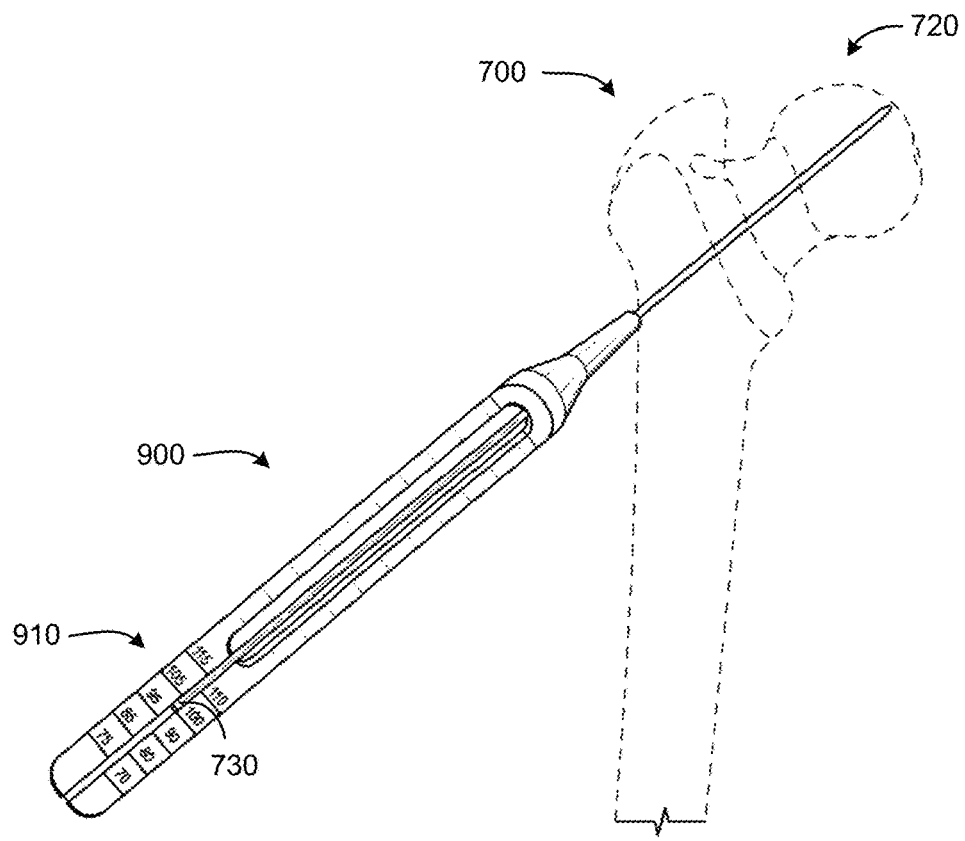
FIG. 14 illustrates a side view of a guide pin depth gauge adjacent a femur, according to an embodiment of the present disclosure.
Figure 15:
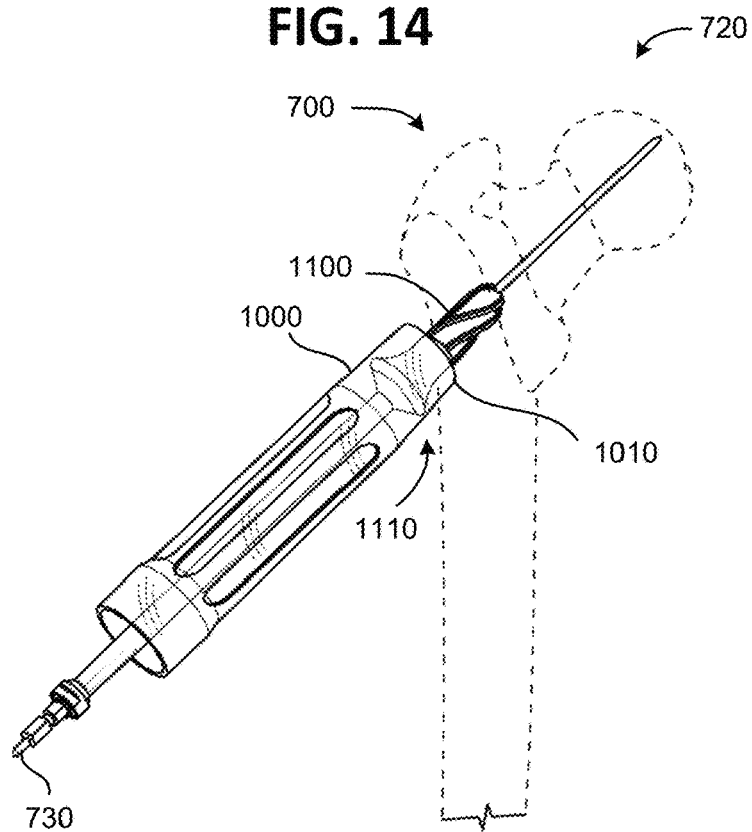
FIG. 15 illustrates a side view of a tissue shield and reamer adjacent a femur, according to embodiments of the present disclosure.

FIG. 14 illustrates a side view of a guide pin depth gauge 900 adjacent the femur 700 in order to measure a depth of the guide pin 730 inside the femur 700. The guide pin depth gauge 900 may include one or more markings 910 configured to indicate a depth of the guide pin 730 inside the femur 700, which may then be utilized to determine a selected length for the femoral fastener 300.

Once the depth of the guide pin 730 has been determined, a reamer 1100 and a tissue shield 1000 may be placed adjacent the femur 700 in order to ream a bone tunnel in the femur 700 that may be configured to receive the barrel 405 of the femoral support member 400 therein.

In some embodiments, a distal end 1010 of the tissue shield 1000 may be notched to conform to a lateral side of the femur 700.

In some embodiments, the reamer 1100 may include a flared portion 1110 that may be configured to provide a countersink in the femur to receive the base 440 of the barrel 405 therein (see FIG. 4D).

Figure 16:
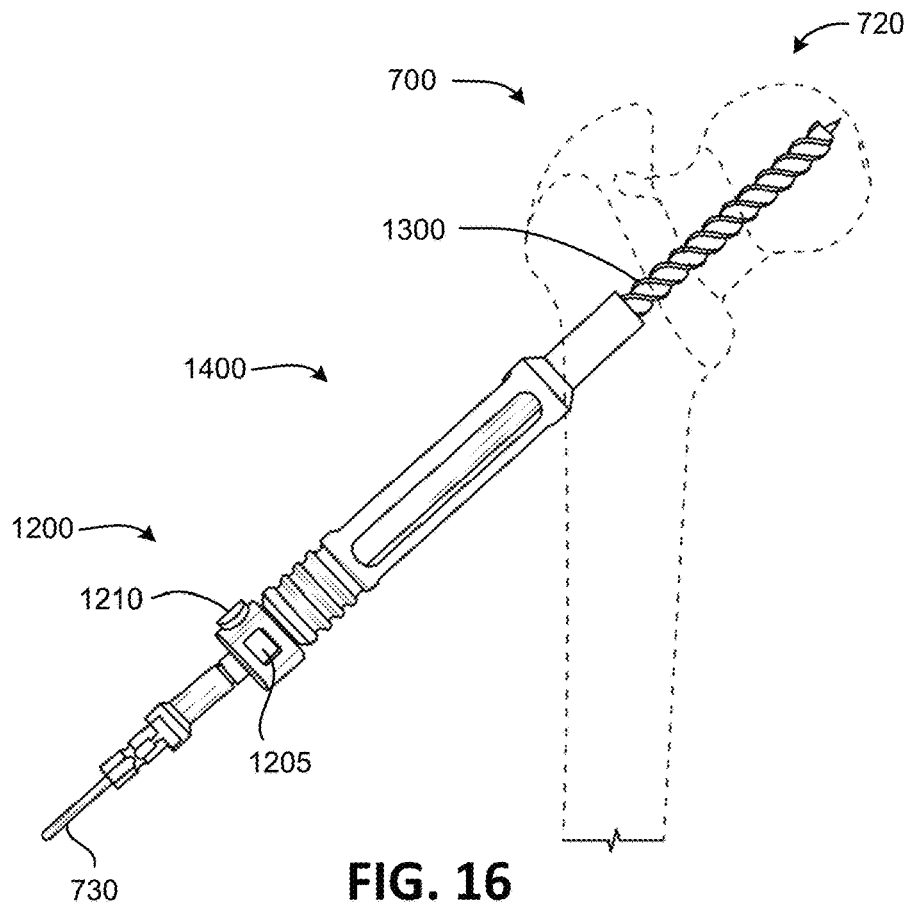
FIG. 16 illustrates a side view of drill bit, adjustable depth stop, and centering sleeve, according to embodiments of the present disclosure.

FIG. 16 illustrates a side view of drill bit 1300, an adjustable depth stop 1200, and centering sleeve 1400, according to embodiments of the present disclosure. The adjustable depth stop 1200 may be slid onto the drill bit 1300 while depressing the button 1210 on the adjustable depth stop 1200 until a previously measured femoral fastener length is seen in the window 1205. The button 1210 may then be released in order to couple the adjustable depth stop 1200 to the drill bit 1300 and hold its position. The centering sleeve 1400 may be slid over the drill bit 1300. The drill bit 1300 and centering sleeve 1400 may then be placed over the guide pin 730. The centering sleeve 1400 may be slid down the guide pin 730 until seated, and the drill bit 1300 may then be rotated to form a bone tunnel for the femoral fastener 300. The drill bit 1300 may be advanced until the adjustable depth stop 1200 rests against the centering sleeve 1400. This may indicate that the bone tunnel has been formed to a proper depth corresponding to the depth shown in the window 1205 of the adjustable depth stop 1200.

Figure 17:
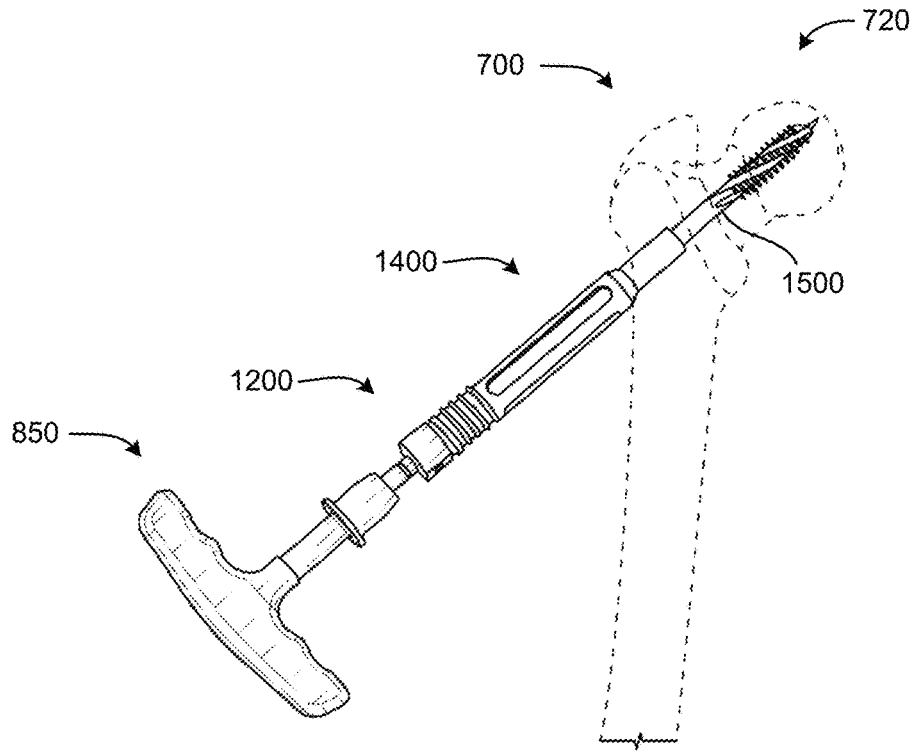
FIG. 17 illustrates a side view of a tap device, according to an embodiment of the present disclosure.

FIG. 17 illustrates a side view of a tap 1500, according to an embodiment of the present disclosure. The adjustable depth stop 1200 may be placed on the tap 1500 in the same manner as the drill bit 1300 described above. The tap 1500 and centering sleeve 1400 may then be placed over the guide pin 730 and advanced into the femur. The tap 1500 may then be rotated using the handle 850 to form a tapped bone thread about the bone tunnel in the head 720 of the femur 700. The tapped bone thread may be configured to receive the helical thread 310 of the femoral fastener 300 therein.

In some embodiments, the tap 1500 may be configured to pre-form threading in the femur 700 according to any threading shape that is disclosed herein. In this manner, taps with any suitable shape may be utilized in conjunction with any fastener described or contemplated herein to match or substantially match the threading geometry of a given fastener.

Figure 18A:
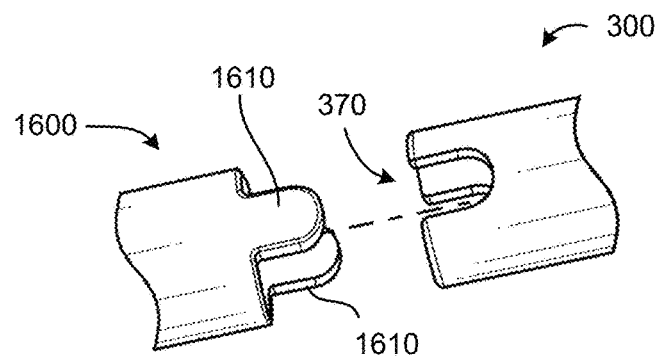
FIG. 18A illustrates a close up partial view of a connection feature between an inserter and a femoral fastener prior to engagement, according to an embodiment of the present disclosure.
Figure 18B:
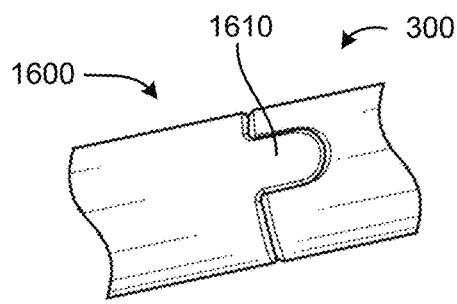
FIG. 18B illustrates a side view of the connection feature of FIG. 18A after engagement.
Figure 18C:
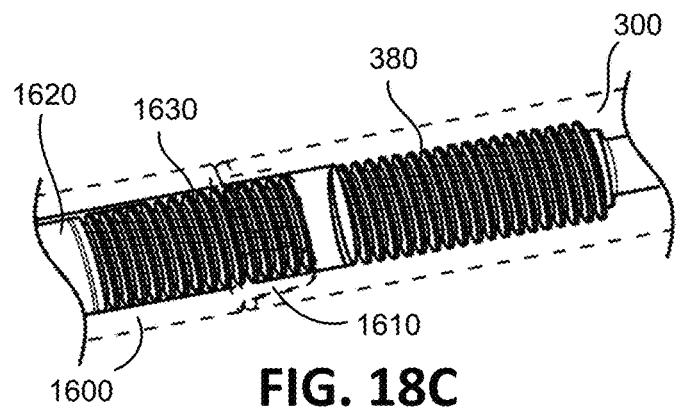
FIG. 18C illustrates a side view of the connection feature of FIG. 18A showing an inserter coupler that is inside the inserter before it engages with an internal thread of the femoral fastener.
Figure 18D:
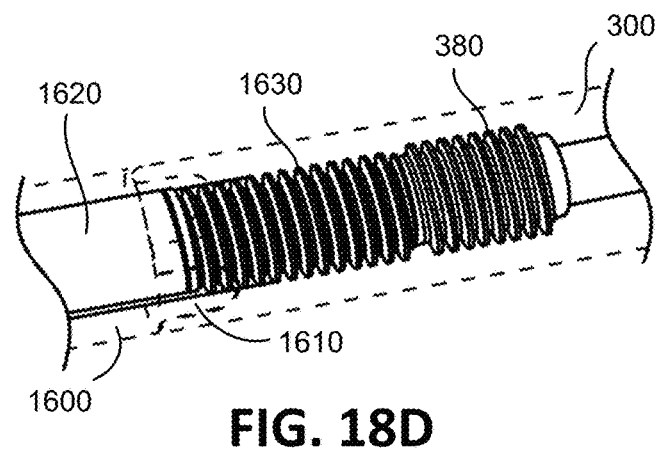
FIG. 18D illustrates a side view of the connection feature of FIG. 18C after the inserter coupler has been engaged with the internal thread of the femoral fastener.

FIGS. 18A-18D illustrate a connection feature formed between an inserter tool 1600 and the femoral fastener 300, according to an embodiment of the present disclosure. Specifically, FIG. 18A is a close up partial view of the connection feature between the inserter tool 1600 and the femoral fastener 300 prior to engagement; FIG. 18B is a side view of the connection feature of FIG. 18A after engagement; FIG. 18C is a side view of the connection feature showing an inserter coupler 1620 inside the inserter tool 1600 before it engages with the internal thread 380 of the femoral fastener 300; and FIG. 18D illustrates a side view of the connection feature after the external thread 1630 of the inserter coupler 1620 engages the internal thread 380 of the femoral fastener 300 to retain the femoral fastener 300 to the inserter tool 1600. As shown in FIGS. 18A-18B, the inserter tool 1600 may include one or more projections 1610 that may be received within the one or more recesses 370 of the femoral fastener 300. In this manner, the femoral fastener 300 may be coupled with the inserter tool 1600 to facilitate insertion of the femoral fastener 300 into the bone tunnel formed in the femur 700.

Figure 19:
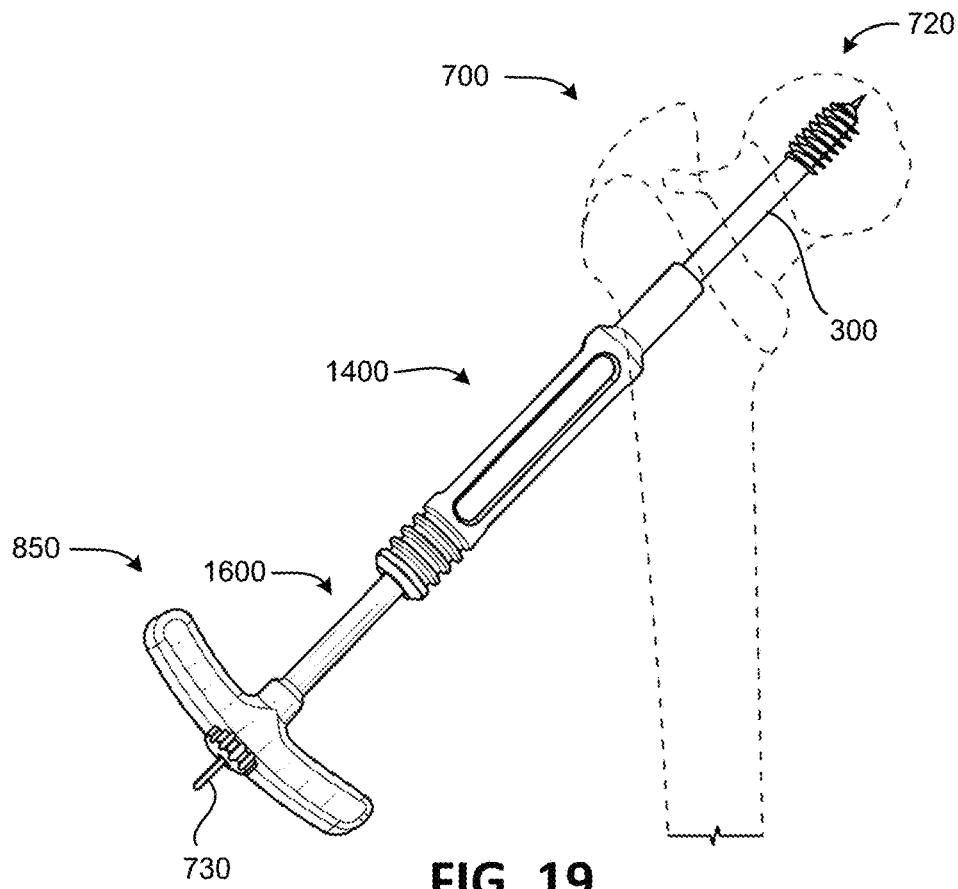
FIG. 19 illustrates a side view of a centering sleeve and inserter facilitating placement of a femoral fastener within a femur.

FIG. 19 illustrates a side view of the centering sleeve 1400 and the inserter tool 1600 facilitating placement of the femoral fastener 300 within the femur 700.

In some embodiments, a portion of the shaft 305 of the femoral fastener 300 comprising the helical thread 310 may be placed within the head 720 of the femur 700, such that, a concave undercut surface of the helical thread 310 may be positioned within the head 720 of the femur 700 to transmit at least one force from the head 720 of the femur 700 to the neck 710 of the femur 700.

In some embodiments, placing the a portion of the shaft 305 comprising the helical thread 310 within the head 720 of the femur 700 comprises rotating the shaft 305 to insert the helical thread 310 into a tapped bone thread that is disposed about the bone tunnel.

Figure 20:
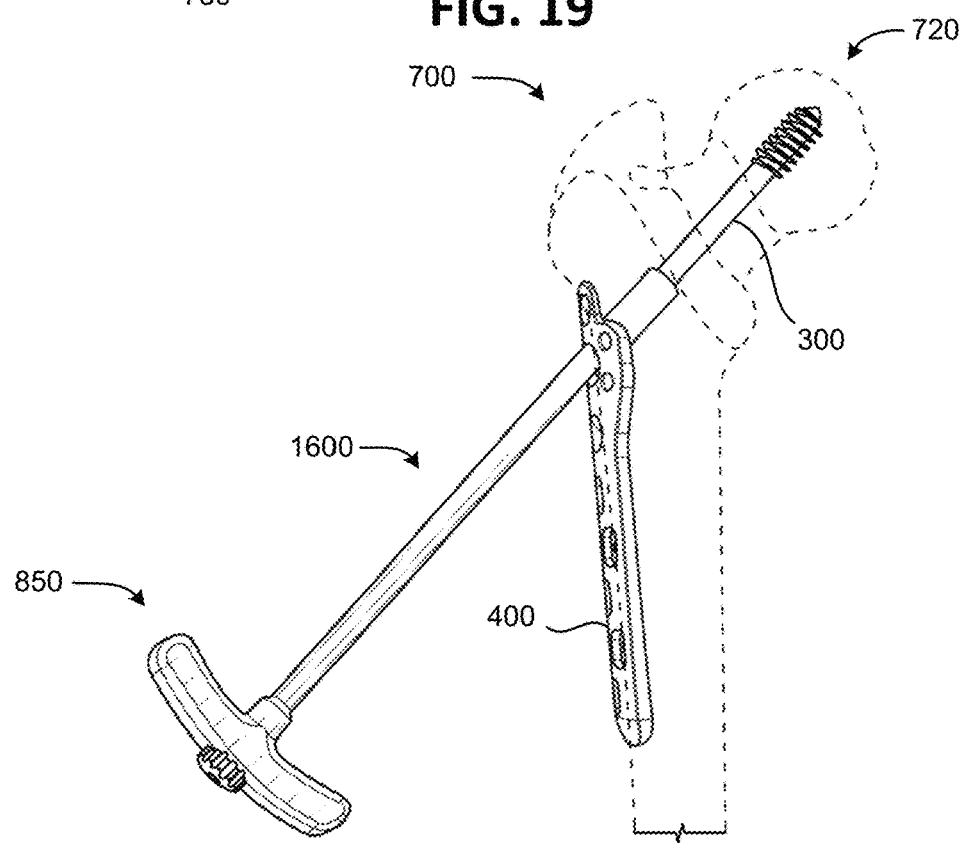
FIG. 20 illustrates a side view of the inserter of FIG. 19 being utilized to couple a femoral support member to the femoral fastener.

FIG. 20 illustrates a side view of the inserter tool 1600 facilitating placement of the femoral support member 400 against the femur 700 with the proximal end 301 of the shaft 305 of the femoral fastener 300 placed inside the passageway 410 of the barrel 405.

Thus, in some embodiments, the proximal end 301 of the shaft 305 of the femoral fastener 300 may be inserted into the first opening 411 of the passageway 410 formed through the femoral support member 400 when the femoral support member 400 is oriented with respect to the longitudinal axis of the femoral bone.

Moreover, in some embodiments the distal end 502 of the stop member 500 may be inserted into the second opening 412 of the passageway 410 opposite the first opening 411, such that a space 610 having a predetermined length 605 may be formed within the passageway 410 between the distal end 502 of the stop member 500 and the proximal end 301 of the shaft 305 based on the preselected length 505 of the stop member 500 or stop member projection 510. In some embodiments, the stop member 500 may be placed within the passageway 410 after the femoral support member 400 has been secured to the femur 700 (e.g., see FIGS. 26-34B).

Figure 21:
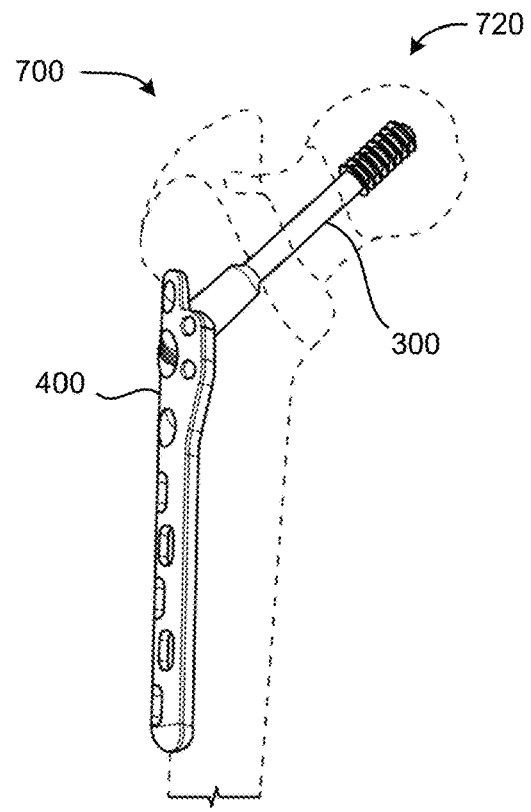
FIG. 21 illustrates a side view the femoral support member and femoral fastener after the inserter has been removed.

FIG. 21 illustrates a side view the femoral support member 400, the femoral fastener 300, and the femur 700 after the inserter tool 1600 has been removed.

Figure 22:
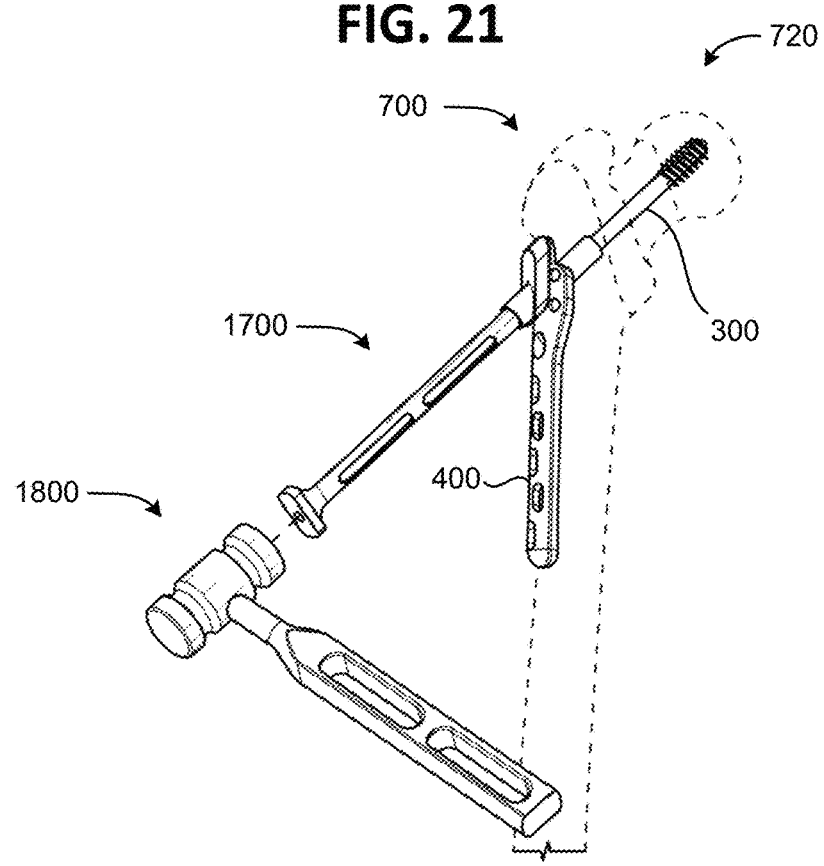
FIG. 22 illustrates a side view of an impactor and mallet utilized to seat the femoral support member against the femur.

FIG. 22 illustrates a side view of an impactor 1700 and a mallet 1800 that may be utilized to further seat the femoral support member 400 against the femur 700, in some embodiments.

Figure 23A:
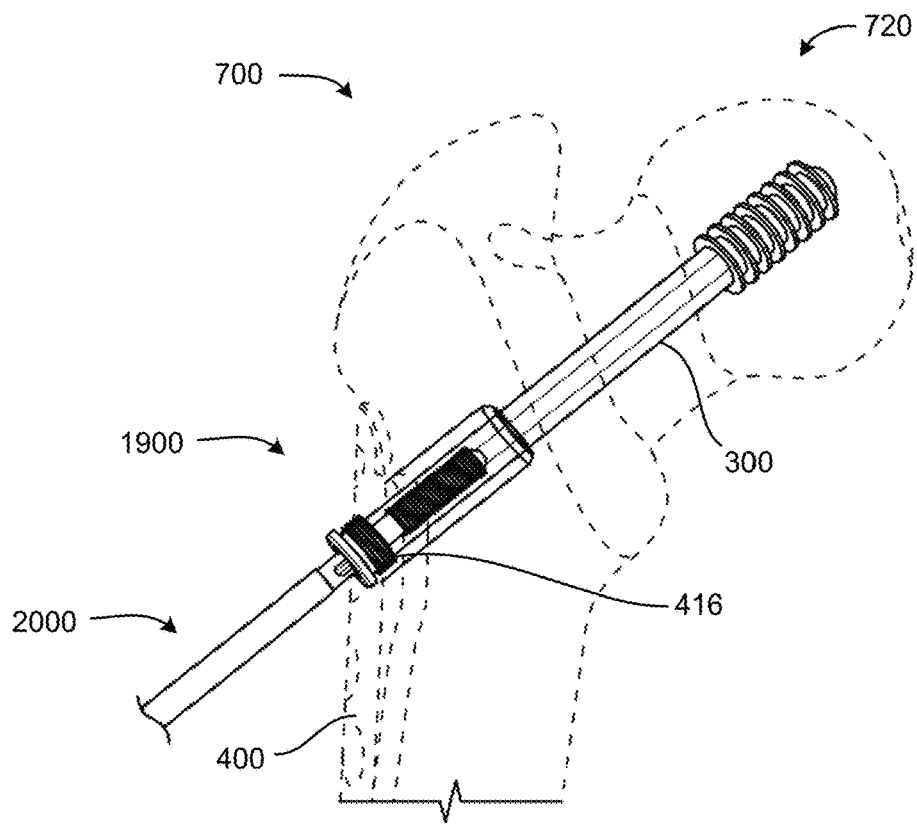
FIG. 23A illustrates a side view of a compression screw inserted into the femoral support member and the femoral fastener.
Figure 23B:
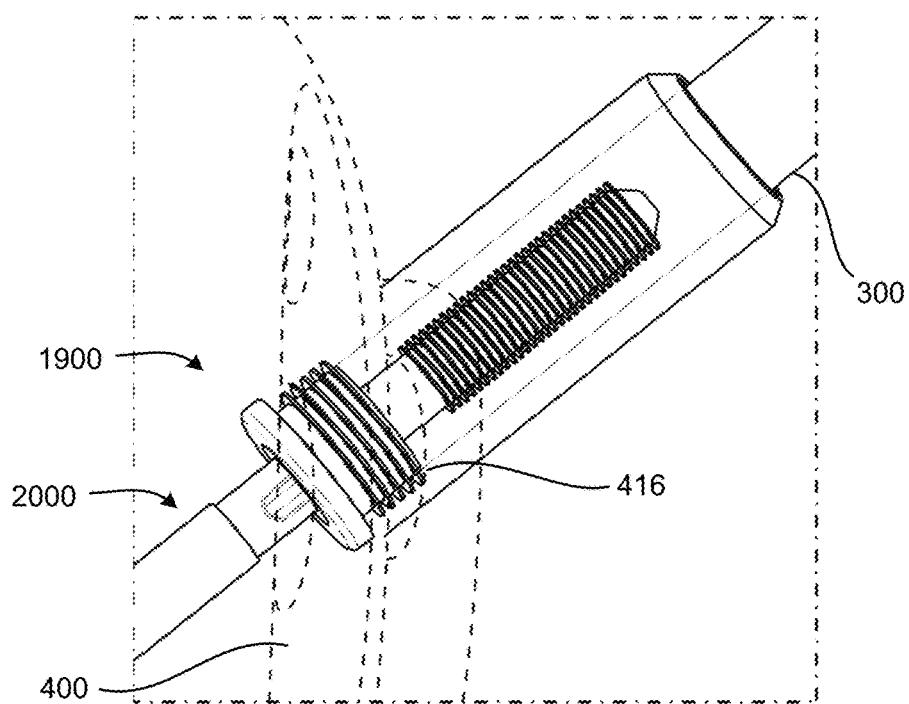
FIG. 23B illustrates a close-up view of the compression screw shown in FIG. 23A.

FIG. 23A illustrates a side view of a compression screw 1900 being inserted into the femoral support member 400 and the femoral fastener 300 with a driver tool 2000, according to an embodiment of the present disclosure. FIG. 23B illustrates a close-up view of the compression screw 1900 shown in FIG. 23A. If desired, the compression screw 1900 may be utilized to generate a compression force across a fracture of the femur 700 by threading the compression screw 1900 into the femoral fastener 300 while a head of the compression screw 1900 presses against the barrel shoulder 416 in the passageway 410. The compression screw 1900 may be rotated until a desired compression force is achieved. To maintain the compression force, one or more support fasteners 2800 (e.g., see FIG. 29) may then be placed across the fracture while the compression screw 1900 is generating the compression force. The compression screw 1900 may then be removed after compression has been achieved and maintained by the one or more support fasteners 2800. However, in some embodiments the compression screw 1900 may left inside the femoral fixation assembly 600.

Figure 24:
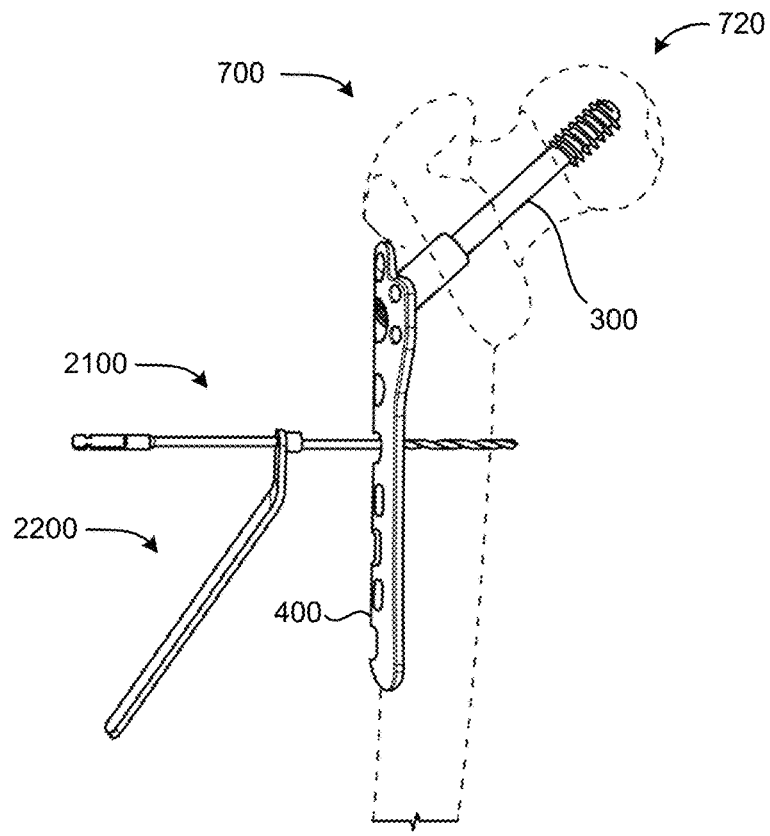
FIG. 24 illustrates a side view of a drill bit and drill bit guide forming bone tunnels in the femur, according to an embodiment of the present disclosure.
Figure 25:
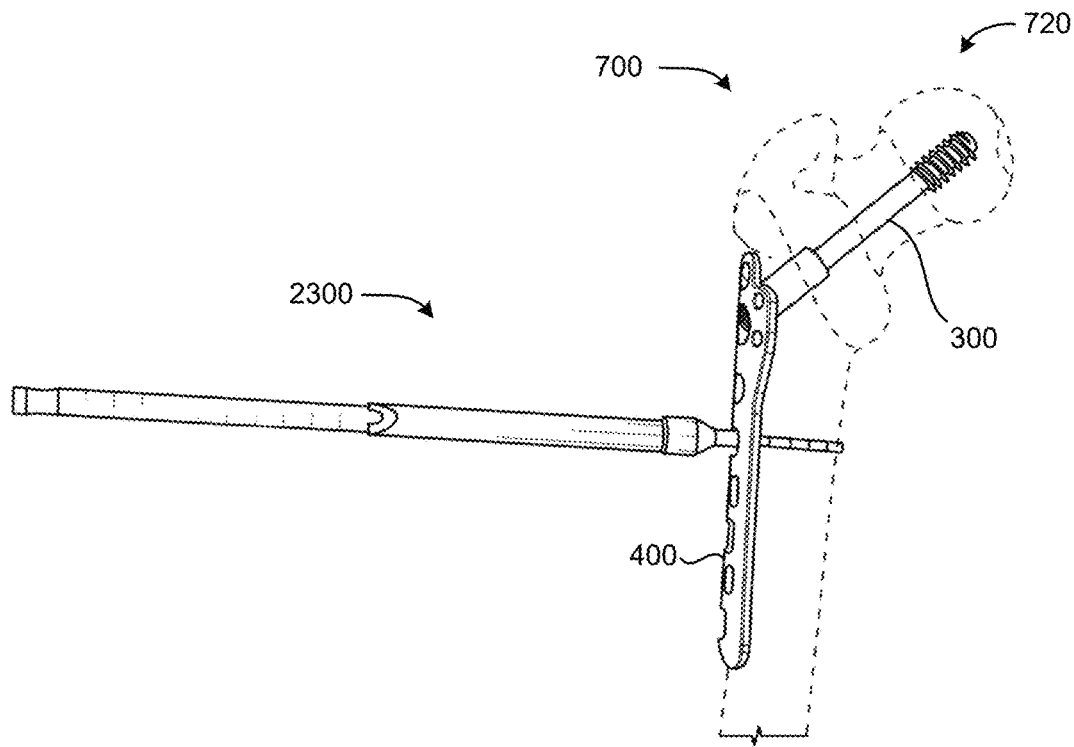
FIG. 25 illustrates a side view of a depth gauge utilized to measure a depth of a bone tunnel, according to an embodiment of the present disclosure.
Figure 26:
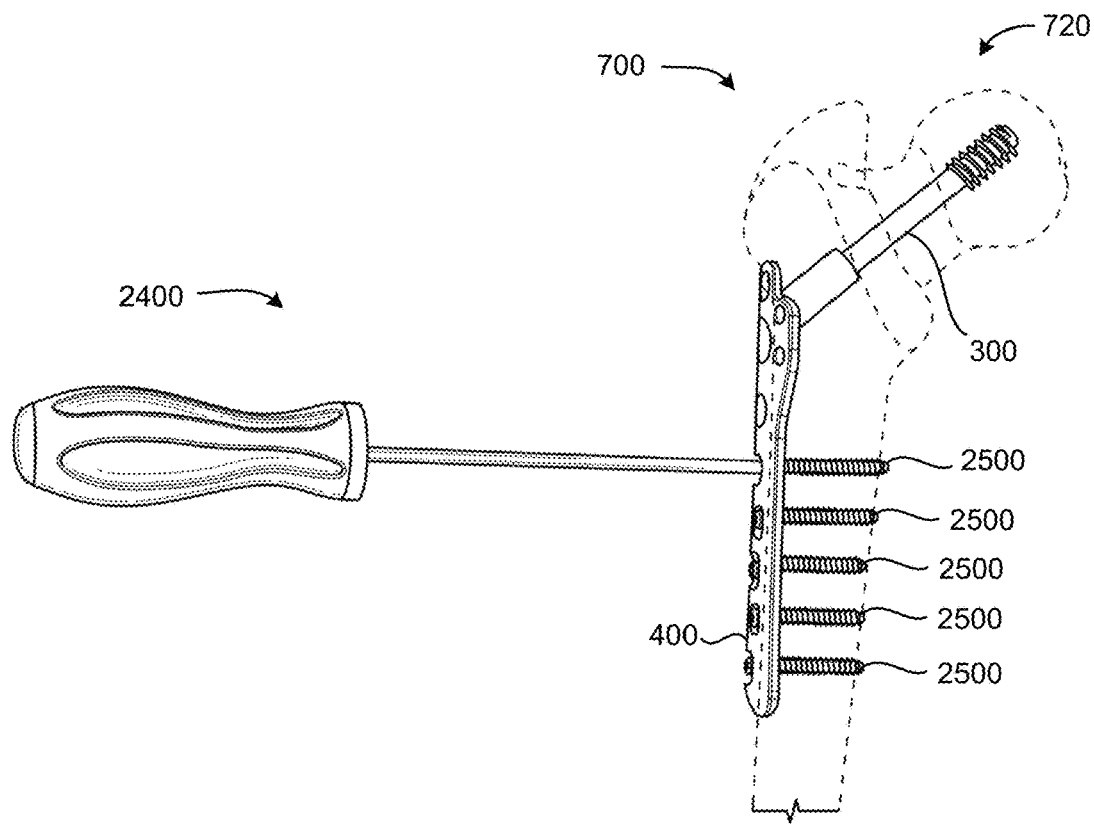
FIG. 26 illustrates a side view of a driver installing one or more bone plate fasteners into the femur, according to an embodiment of the present disclosure.
Figure 27:
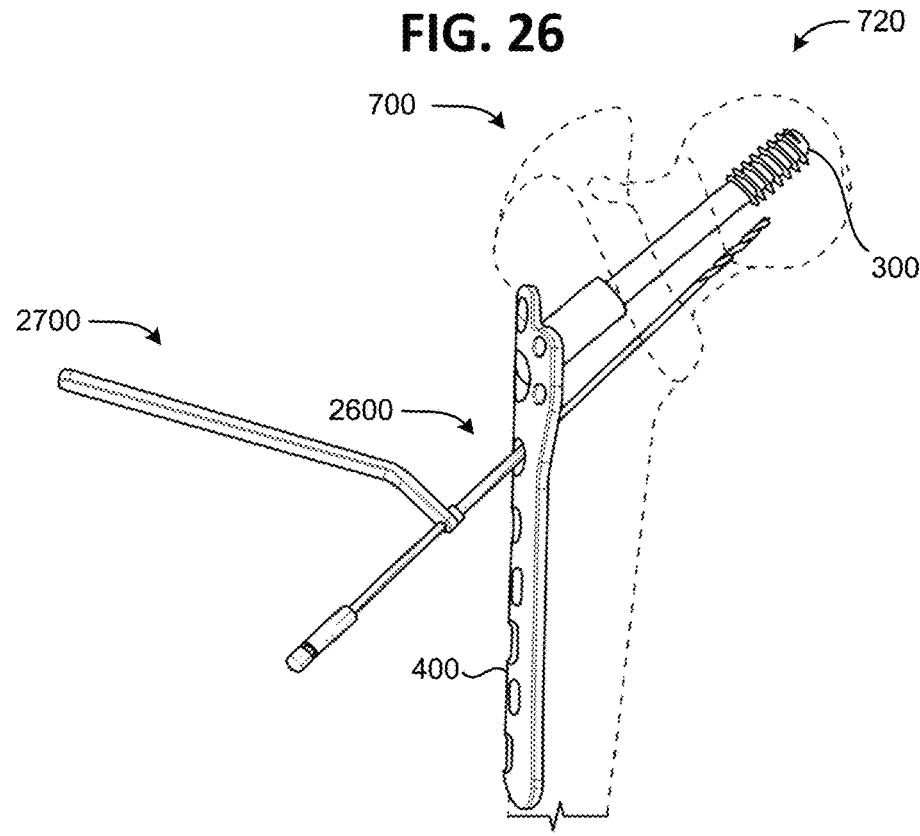
FIG. 27 illustrates a side view of a drill bit and drill bit guide forming bone tunnels into the head of the femur, according to another embodiment of the present disclosure.
Figure 28:
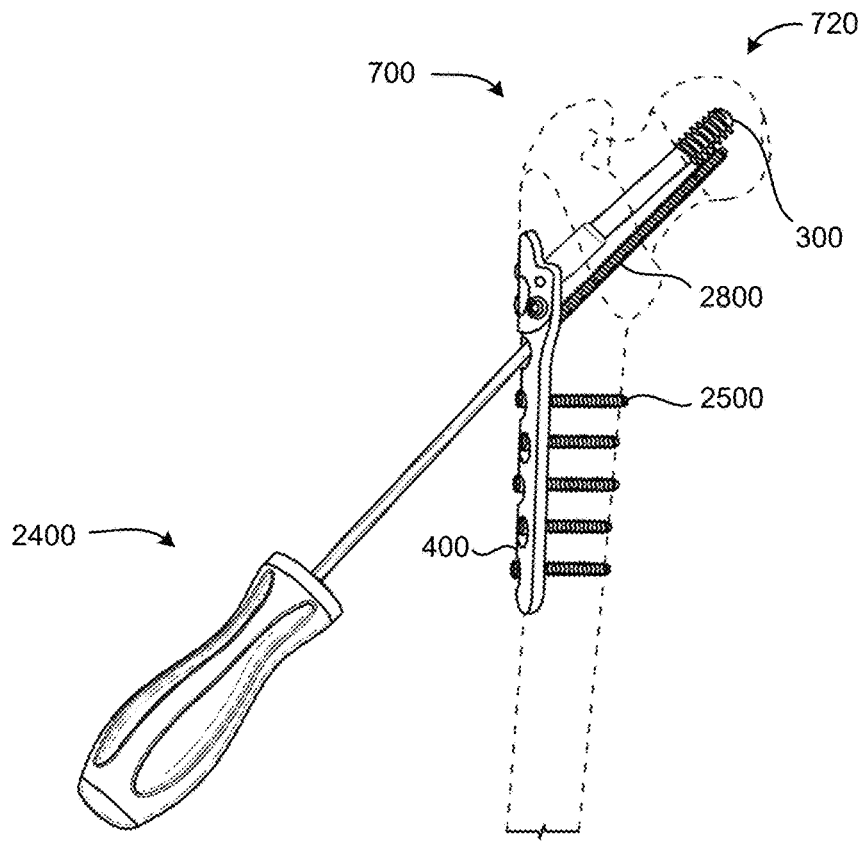
FIG. 28 illustrates a side view of driver installing one or more support fasteners into the head of the femur.
Figure 29:
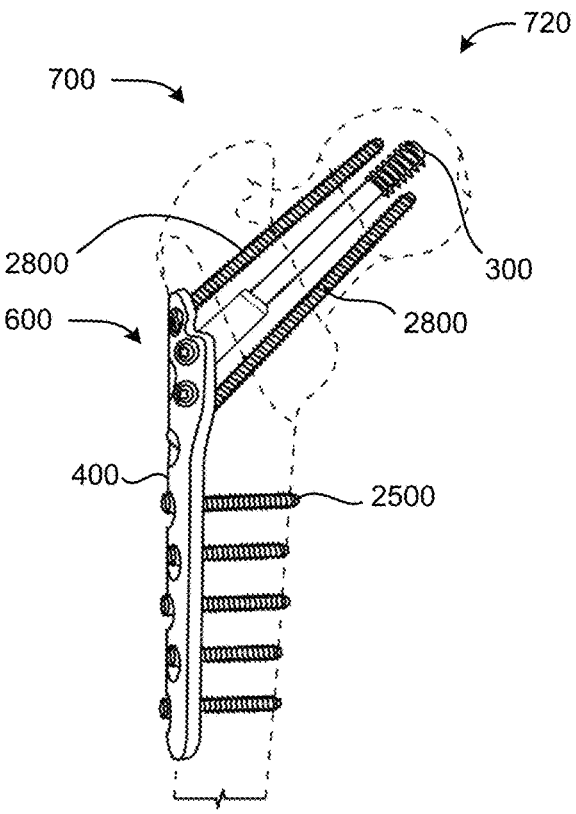
FIG. 29 illustrates a side view of the femoral fixation assembly of FIG. 28 after the one or more support fasteners have been installed.

FIGS. 24-29 illustrate the installation of various bone screws to affix the femoral fixation assembly 600 to the femur 700. Specifically, FIG. 24 illustrates a side view of a drill bit 2100 and a drill bit guide 2200 forming one or more bone tunnels in the femur 700; FIG. 25 illustrates a side view of a depth gauge 2300 measuring a depth of a bone tunnel to ascertain a required length for a bone screw; FIG. 26 illustrates a side view of a driver tool 2400 installing one or more bone plate fasteners 2500 into the femur 700; FIG. 27 illustrates a side view of a drill bit 2600 and drill bit guide 2700 forming a bone tunnel into the head 720 of the femur 700; FIG. 28 illustrates a side view of a driver tool 2400 installing one or more support fasteners 2800 into the head 720 of the femur 700; and FIG. 29 illustrates a side view of the femoral fixation assembly 600 after the one or more support fasteners 2800 have been installed.

Figure 30:
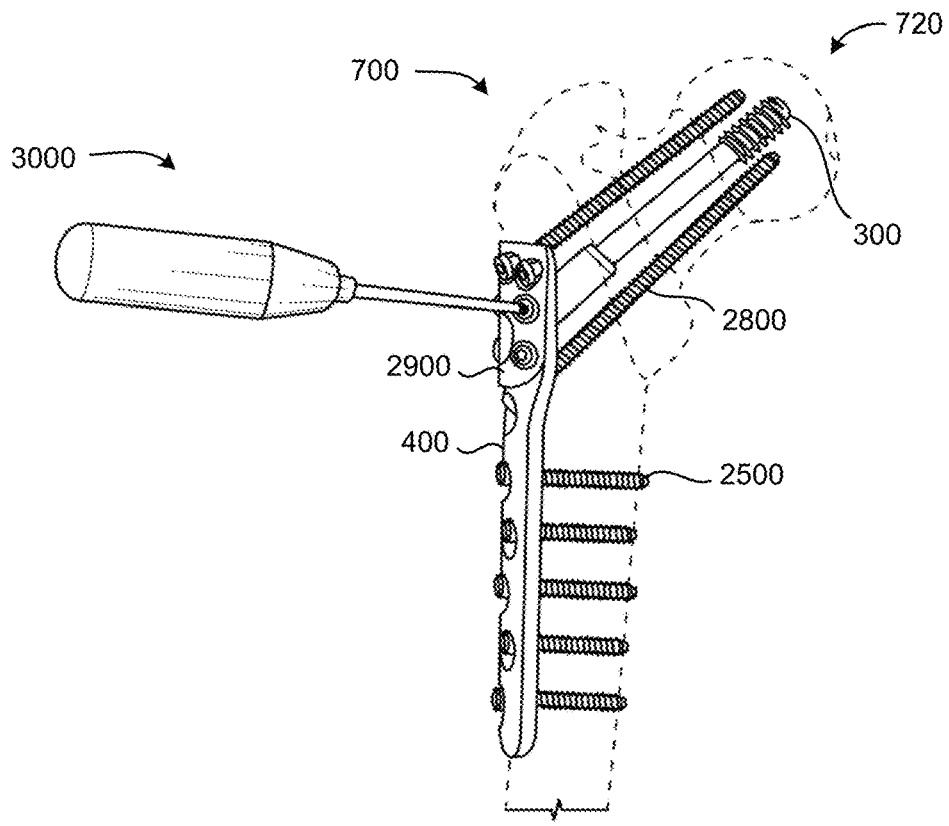
FIG. 30 illustrates a side view of an extension plate being coupled to the femoral support member, according to an embodiment of the present disclosure.
Figure 31:
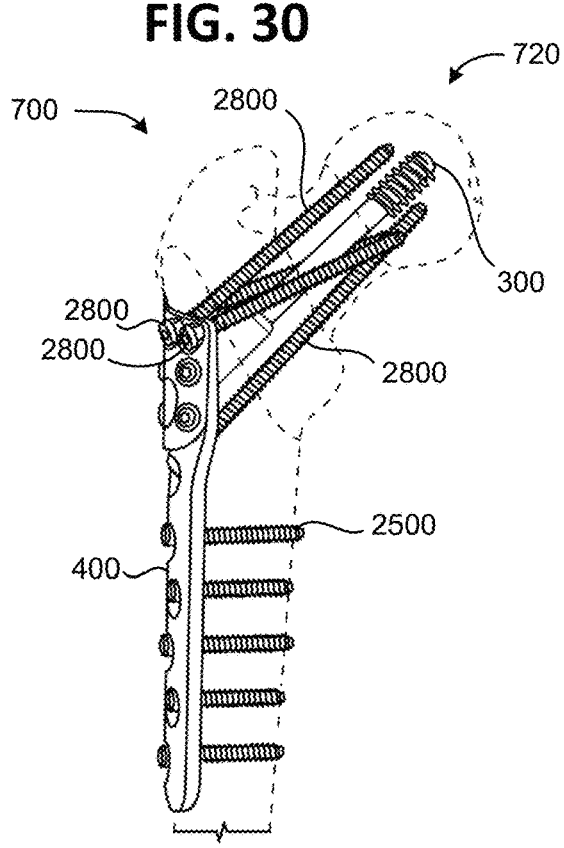
FIG. 31 illustrates a side view of the femoral fixation assembly of FIG. 30 after the extension plate has been coupled to the femoral support member and additional support fasteners have been inserted into the head of the femur.

FIG. 30 illustrates a side view of an extension plate 2900 being coupled to the femoral support member 400 with a driver tool 3000, according to some embodiments of the present disclosure. FIG. 31 illustrates a side view of the femoral fixation assembly 600 after the extension plate 2900 has been coupled to the femoral support member 400 and support fasteners 2800 have been inserted into the head 720 of the femur 700 through the extension plate 2900.

Figure 32:
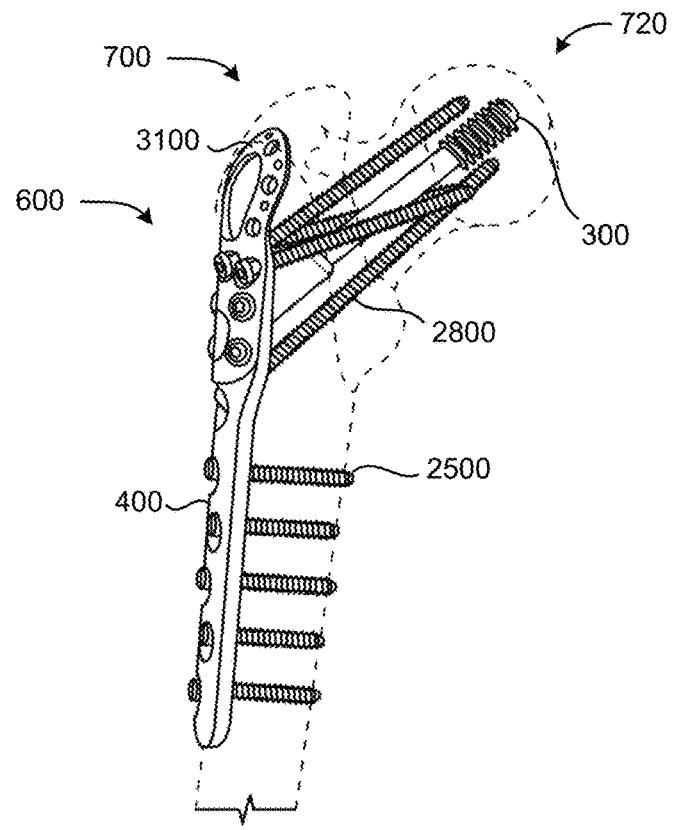
FIG. 32 illustrates a side view of the femoral fixation assembly of FIG. 29 after a trochanter plate has been coupled to the femoral support member and additional support fasteners have been inserted into the head of the femur, according to another embodiment of the present disclosure.
Figure 33:
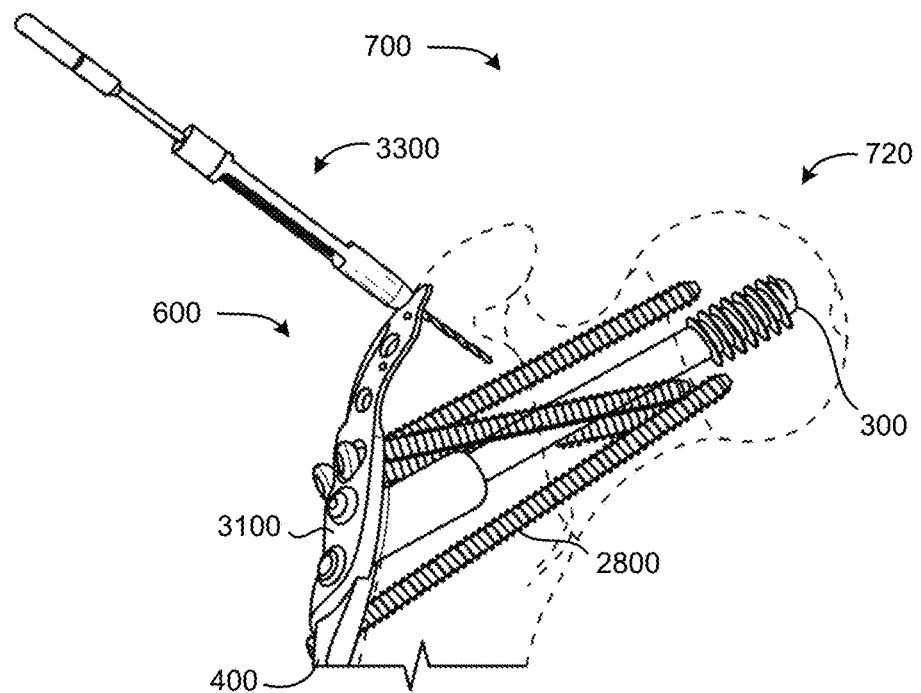
FIG. 33 illustrates a side view of the femoral fixation assembly of FIG. 32 showing a drill bit forming one or more bone tunnels to receive one or more trochanter plate fasteners to secure the trochanter plate to the femur.
Figure 34A:
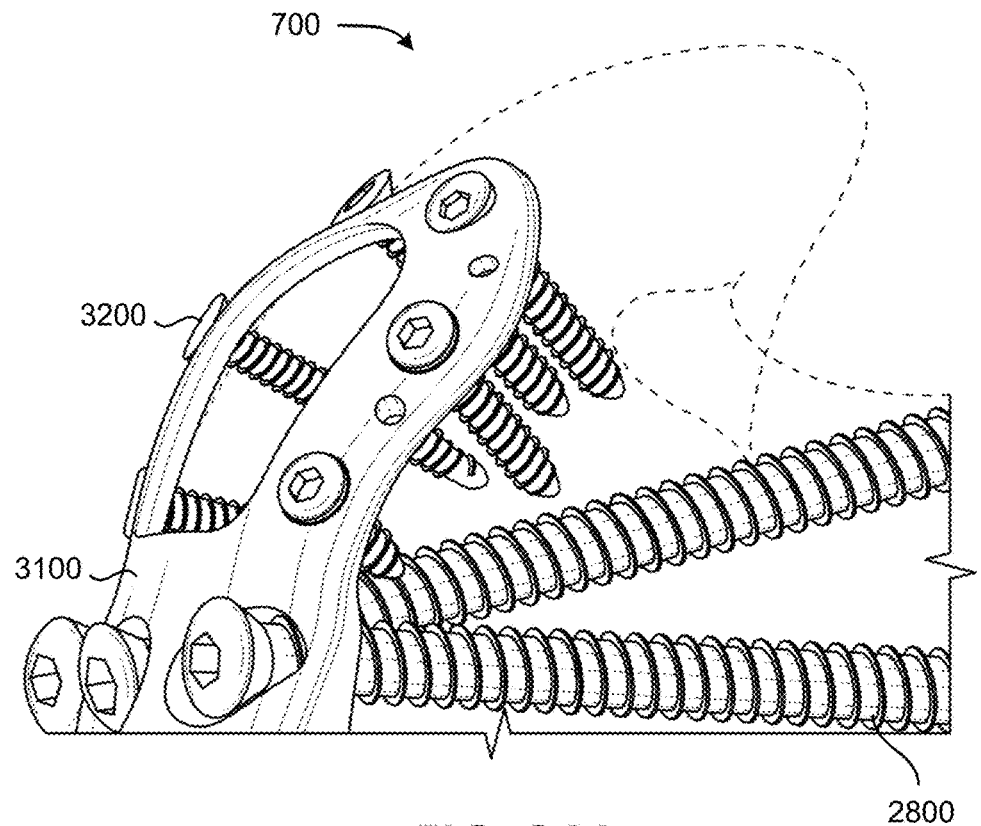
FIG. 34A illustrates a perspective side view of the femoral fixation assembly shown in FIG. 33 after the one or more trochanter plate fasteners have been installed.
Figure 34B:
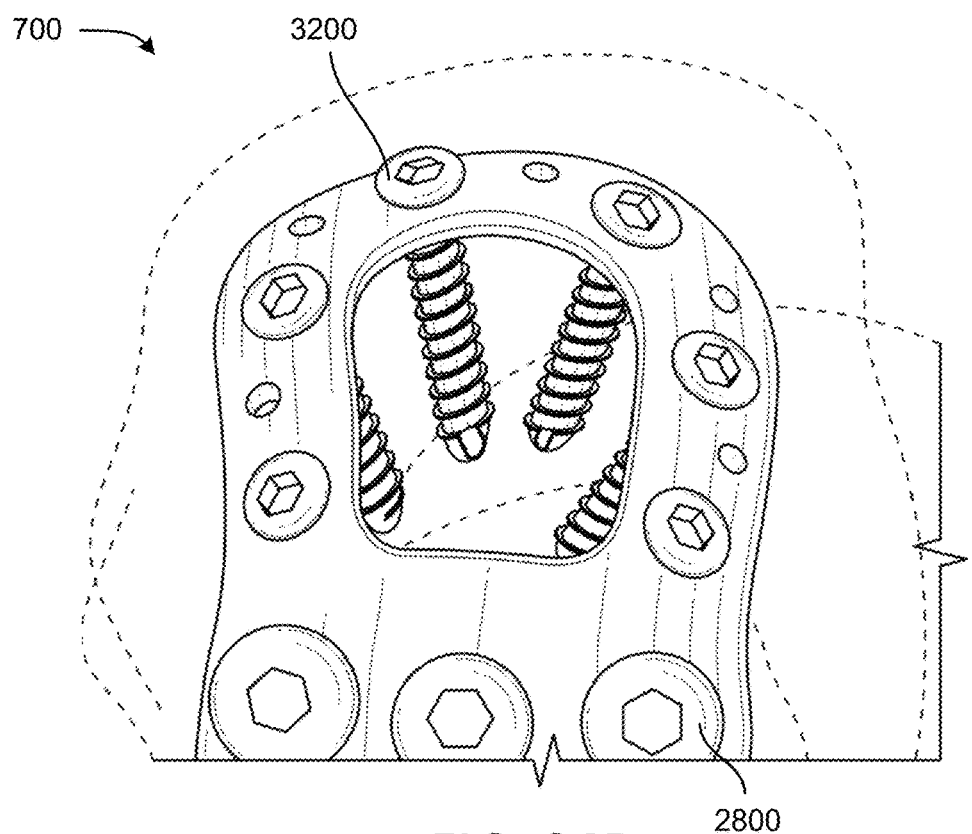
FIG. 34B illustrates a perspective front view of the femoral fixation assembly shown in FIG. 34A.

FIGS. 32-34B illustrate installation of a trochanter plate 3100 to the femur 700, according to some embodiments of the present disclosure. Specifically, FIG. 32 illustrates a side view of the femoral fixation assembly 600 after a trochanter plate 3100 has been coupled to the femoral support member 400 and additional support fasteners 2800 have been inserted into the head 720 of the femur 700 through the trochanter plate 3100; FIG. 33 illustrates a side view of the femoral fixation assembly 600 with a drill bit 3300 forming one or more bone tunnels in the femur 700 to receive one or more trochanter plate fasteners 3200 to secure the trochanter plate 3100 to the femur 700; FIG. 34A illustrates a perspective side view of the femoral fixation assembly 600 after the one or more trochanter plate fasteners 3200 have been installed into the femur 700 through the trochanter plate 3100; and FIG. 34B illustrates a front view of the femoral fixation assembly 600 of FIG. 34A.

Any procedures/methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Any of the fasteners described herein may be configured for removal and replacement during a revision procedure by simply unscrewing and removing the fastener from the bone/tissue in which the fastener resides. Moreover, the fasteners described herein may advantageously be removed from bone without removing any appreciable amount of bone during the removal process to preserve the bone. In this manner, implants may be mechanically integrated with the bone, while not being cemented to the bone or integrated via bony ingrowth, in order to provide an instant and removable connection between an implant and a bone. Accordingly, revision procedures utilizing the fasteners described herein can result in less trauma to the bone and improved patient outcomes.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, drawing, or description thereof for the purpose of streamlining the present disclosure. This method of disclosure, however, is not to be interpreted as reflecting an intention that any embodiment requires more features than those expressly recited in that embodiment. Rather, inventive aspects lie in a combination of fewer than all features of any single foregoing disclosed embodiment.

Recitation of the term "first" with respect to a feature or element does not necessarily imply the existence of a second or additional such feature or element. Elements recited in means-plus-function format are intended to be construed in accordance with 35 U.S.C. § 112(f). It will be apparent to those having skill in the art that changes may be made to the details of the above-described embodiments without departing from the underlying principles set forth herein.

The phrases "connected to," "coupled to," and "in communication with" refer to any form of interaction between two or more entities, including mechanical, electrical, magnetic, electromagnetic, fluid, and thermal interaction. Two components may be functionally coupled to each other even though they are not in direct contact with each other. The term "coupled" can include components that are coupled to each other via integral formation, as well as components that are removably and/or non-removably coupled with each other. The term "abutting" refers to items that may be in direct physical contact with each other, although the items may not necessarily be attached together. The phrase "fluid communication" refers to two or more features that are connected such that a fluid within one feature is able to pass into another feature. Moreover, as defined herein the term "substantially" means within +/−20% of a target value, measurement, or desired characteristic.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the devices, systems, and methods disclosed herein.

What is claimed is:

1. A femoral fixation assembly comprising:
   a femoral fastener comprising:
      a shaft comprising:
         a proximal end;
         a distal end;
         a longitudinal axis; and
         a minor diameter, wherein the minor diameter of the shaft is constant over a length of the shaft intermediate the proximal end and the distal end of the shaft; and
      a helical thread disposed about the shaft along the longitudinal axis between a first location and a second location along the shaft, the helical thread comprising a concave undercut surface; and
   a femoral support member comprising:
      a proximal end;
      a distal end;
      a longitudinal axis; and
      a passageway formed through the femoral support member at an angle with respect to the longitudinal axis of the femoral support member;
   wherein, when the femoral fastener is implanted within a neck and a head of a femoral bone, and the femoral support member is implanted along a longitudinal axis of the femoral bone:
      at least a portion of the shaft is slidingly received within the passageway of the femoral support member; and
      the concave undercut surface is oriented toward the proximal end of the femoral fastener and configured to transmit at least one force from the head of the femoral bone to the neck of the femoral bone.

2. The femoral fixation assembly of claim 1, wherein the concave undercut surface comprises at least one substantially flat surface.

3. The femoral fixation assembly of claim 2, wherein the concave undercut surface comprises a plurality of flat surfaces that are angled relative to each other.

4. The femoral fixation assembly of claim 3, when the femoral fastener is viewed in section along a plane intersecting the longitudinal axis of the shaft, the concave undercut surface comprises at least one chevron shape oriented toward the proximal end of the shaft.

5. The femoral fixation assembly of claim 1, wherein the concave undercut surface comprises at least one curved surface.

6. The femoral fixation assembly of claim 5, wherein, when the femoral fastener is viewed in section along a plane intersecting the longitudinal axis of the shaft, the concave undercut surface comprises at least one partial crescent shape oriented toward the proximal end of the shaft.

7. The femoral fixation assembly of claim 1, wherein, when the femoral fastener is viewed in section along a plane intersecting the longitudinal axis of the shaft, the concave undercut surface comprises at least one bent shape having an intermediate portion that is oriented toward the proximal end of the femoral fastener.

8. The femoral fixation assembly of claim 1, wherein the femoral fastener comprises a non-threaded constant diameter portion proximal to a threaded portion of the femoral fastener.

9. A femoral fixation assembly comprising:
a femoral fastener comprising:
a shaft comprising:
a proximal end;
a distal end; and
a longitudinal axis; and
a helical thread disposed about the shaft along the longitudinal axis between a first location and a second location along the shaft;
a femoral support member comprising:
a proximal end;
a distal end;
a longitudinal axis; and
a passageway comprising:
a first opening; and
a second opening opposite the first opening;
wherein, the passageway is formed through the femoral support member at an angle with respect to the longitudinal axis of the femoral support member; and
a stop member comprising:
a proximal end;
a distal end;
a longitudinal axis; and
a stop member projection having a preselected length;
wherein, when the femoral fastener is implanted within a neck and a head of a femoral bone, and the femoral support member is oriented with respect to a longitudinal axis of the femoral bone:
at least a portion of the shaft is slidingly received within the passageway through the first opening;
at least a portion of the stop member projection is received within the passageway through the second opening; and
a space having a predetermined length is formed within the passageway between the distal end of the stop member projection and the proximal end of the shaft based on the preselected length of the stop member projection, wherein the stop member projection is configured to limit an amount of collapse that may occur to the predetermined length of the space that is defined within the passageway.

10. The femoral fixation assembly of claim 9, wherein the femoral support member comprises a bone plate.

11. The femoral fixation assembly of claim 9, wherein the angle of the passageway with respect to the longitudinal axis of the femoral support member comprises an acute angle.

12. The femoral fixation assembly of claim 9, wherein the preselected length of the stop member projection is chosen such that the predetermined length of the space within the passageway is greater than zero.

13. The femoral fixation assembly of claim 9, wherein the preselected length of the stop member projection is chosen such that the predetermined length of the space within the passageway is zero.

14. The femoral fixation assembly of claim 9, wherein:
the femoral support member further comprises a passageway shoulder; and
the stop member further comprises a stop member shoulder,
wherein:
the stop member shoulder is configured to engage the passageway shoulder when the stop member is received within the passageway through the second opening.

15. A femoral fixation assembly comprising:
a femoral fastener comprising:
a shaft comprising:
a proximal end comprising a non-threaded portion having a first diameter;
a distal end; and
a longitudinal axis; and
a helical thread disposed about the shaft along the longitudinal axis between a first location and a second location along the shaft defining a threaded portion therebetween having a second major diameter, the helical thread comprising a concave undercut surface, wherein the first diameter of the non-threaded portion is less than the second major diameter of the threaded portion; and
a femoral support member comprising:
a proximal end;
a distal end;
a longitudinal axis; and
a passageway formed through the femoral support member at an angle with respect to the longitudinal axis of the femoral support member; and
at least one support fastener;
wherein, when the femoral fastener is implanted within a neck and a head of a femoral bone, and the femoral support member is implanted along a longitudinal axis of the femoral bone:
at least a portion of the shaft is slidingly received within the passageway of the femoral support member;
the concave undercut surface is oriented toward the proximal end of the femoral fastener and configured to transmit at least one force from the head of the femoral bone to the neck of the femoral bone; and
the at least one support fastener is configured to be received through at least one aperture formed in the femoral support member for implantation within the neck and head of the femoral bone.

16. The femoral fixation assembly of claim 15 further comprising an extension plate couplable with the femoral support member.

17. The femoral fixation assembly of claim 16, wherein the femoral support member comprises a bone plate and the extension plate is couplable with the bone plate.

18. The femoral fixation assembly of claim 15, wherein the non-threaded portion comprises a constant diameter portion proximal to the threaded portion of the femoral fastener.

19. A femoral fixation assembly comprising:
a femoral fastener comprising:
a shaft comprising:
a proximal end comprising a non-threaded portion having a first length;
a distal end; and
a longitudinal axis; and
a helical thread disposed about the shaft along the longitudinal axis between a first location and a second location along the shaft defining a threaded portion therebetween having a second length, the helical thread comprising a concave undercut surface on a first side of the helical thread, and a convex undercut surface on a second side of the helical thread, wherein the first length of the non-threaded portion is greater than the second length of the threaded portion; and
a femoral support member comprising:
a proximal end;
a distal end;
a longitudinal axis; and
a passageway formed through the femoral support member at an angle with respect to the longitudinal axis of the femoral support member;
wherein, when the femoral fastener is implanted within a neck and a head of a femoral bone, and the femoral support member is implanted along a longitudinal axis of the femoral bone:
at least a portion of the shaft is slidingly received within the passageway of the femoral support member; and
the concave undercut surface is oriented toward the proximal end of the femoral fastener and configured to transmit at least one force from the head of the femoral bone to the neck of the femoral bone.

20. The femoral fixation assembly of claim 19, wherein the non-threaded portion comprises a constant diameter that is positioned proximal to the threaded portion of the femoral fastener.

21. The femoral fixation assembly of claim 20, wherein the constant diameter of the non-threaded portion is less than a major diameter of the threaded portion of the femoral fastener.

22. A femoral fixation assembly comprising:
a femoral fastener comprising:
a shaft comprising:
a proximal end;
a distal end; and
a longitudinal axis; and
a helical thread disposed about the shaft along the longitudinal axis between a first location and a second location along the shaft, the helical thread comprising a concave undercut surface; and
a femoral support member comprising:
a proximal end;
a distal end;
a longitudinal axis; and
a passageway formed through the femoral support member at an angle with respect to the longitudinal axis of the femoral support member; and
at least one support fastener, wherein the femoral fastener comprises a first threaded portion having a first major diameter, and the at least one support fastener comprises a second threaded portion having a second major diameter that is less than the first major diameter of the femoral fastener;
wherein, when the femoral fastener is implanted within a neck and a head of a femoral bone, and the femoral support member is implanted along a longitudinal axis of the femoral bone:
at least a portion of the shaft is slidingly received within the passageway of the femoral support member;
the concave undercut surface is oriented toward the proximal end of the femoral fastener and configured to transmit at least one force from the head of the femoral bone to the neck of the femoral bone; and
the at least one support fastener is configured to be received through at least one aperture formed in the femoral support member for implantation within the neck and head of the femoral bone.

23. The femoral fixation assembly of claim 22, wherein the femoral fastener comprises a non-threaded portion comprising a constant diameter that is positioned proximal to the first threaded portion of the femoral fastener.

24. The femoral fixation assembly of claim 23, wherein the constant diameter of the non-threaded portion is less than the first major diameter of the first threaded portion of the femoral fastener.

25. A femoral fixation assembly comprising:
a femoral fastener comprising:
a shaft comprising:
a proximal end, wherein the proximal end of the shaft is headless;
a distal end; and
a longitudinal axis; and
a helical thread disposed about the shaft along the longitudinal axis between a first location and a second location along the shaft, the helical thread comprising a concave undercut surface on a first side of the helical thread, and a convex undercut surface on a second side of the helical thread; and
a femoral support member comprising:
a proximal end;
a distal end;
a longitudinal axis; and
a passageway formed through the femoral support member at an angle with respect to the longitudinal axis of the femoral support member;
wherein, when the femoral fastener is implanted within a neck and a head of a femoral bone, and the femoral support member is implanted along a longitudinal axis of the femoral bone:
at least a portion of the shaft is slidingly received within the passageway of the femoral support member; and
the concave undercut surface is oriented toward the proximal end of the femoral fastener and configured to transmit at least one force from the head of the femoral bone to the neck of the femoral bone.

26. The femoral fixation assembly of claim 25, wherein the femoral fastener comprises a non-threaded portion comprising a constant diameter that is positioned proximal to a threaded portion of the femoral fastener.

27. The femoral fixation assembly of claim 26, wherein the constant diameter of the non-threaded portion is less than a major diameter of the threaded portion of the femoral fastener.

28. A femoral fixation assembly comprising:
a femoral fastener comprising:
a shaft comprising:
a proximal end;

a distal end; and
a longitudinal axis; and
a helical thread disposed about the shaft along the longitudinal axis between a first location and a second location along the shaft, the helical thread comprising a concave undercut surface on a first side of the helical thread, and a convex undercut surface on a second side of the helical thread; and a femoral support member comprising:
a proximal end;
a distal end;
a longitudinal axis; and
a barrel comprising a passageway formed therethrough, the barrel extending medially from the femoral support member at an angle with respect to the longitudinal axis of the femoral support member;
wherein, when the femoral fastener is implanted within a neck and a head of a femoral bone, and the femoral support member is implanted along a longitudinal axis of the femoral bone:
at least a portion of the shaft is slidingly received within the passageway of the barrel extending medially from the femoral support member; and
the concave undercut surface is oriented toward the proximal end of the femoral fastener and configured to transmit at least one force from the head of the femoral bone to the neck of the femoral bone.

29. The femoral fixation assembly of claim 28, wherein the angle of the barrel extending medially from the femoral support member with respect to the longitudinal axis of the femoral support member comprises an acute angle.

30. The femoral fixation assembly of claim 28, wherein the femoral fastener comprises a non-threaded portion comprising a constant diameter that is positioned proximal to a threaded portion of the femoral fastener.

31. The femoral fixation assembly of claim 30, wherein the constant diameter of the non-threaded portion is less than a major diameter of the threaded portion of the femoral fastener.

\* \* \* \* \*

UNITED STATES PATENT AND TRADEMARK OFFICE
CERTIFICATE OF CORRECTION

PATENT NO. : 12,121,271 B2  
APPLICATION NO. : 17/468806  
DATED : October 22, 2024  
INVENTOR(S) : Raymond White et al.

Page 1 of 1

It is certified that error appears in the above-identified patent and that said Letters Patent is hereby corrected as shown below:

On the Title Page

(72) Inventors
Raymond White, Windham, ME (US); Matthew Camuso, Falmouth, ME (US); Corey Johnson, Rochester, MN (US); Andrew Fauth, North Logan, UT (US) should read -- Raymond White, Windham, ME (US); Matthew Camuso, Falmouth, ME (US); Corey Johnson, Rochester, MN (US); Andrew Fauth, North Logan, UT (US); Timothy Weber, Indianapolis IN (US) --

Signed and Sealed this
Eighth Day of April, 2025

Coke Morgan Stewart
*Acting Director of the United States Patent and Trademark Office*